United States Patent [19]

McKnight et al.

[11] Patent Number: 5,840,532
[45] Date of Patent: Nov. 24, 1998

[54] NEURONAL BHLH-PAS DOMAIN PROTEINS

[75] Inventors: Steven L. McKnight; David W. Russell, both of Dallas, Tex.

[73] Assignee: Board of Regents, The University of Texas System, Austin, Tex.

[21] Appl. No.: 785,310

[22] Filed: Jan. 21, 1997

[51] Int. Cl.⁶ ............................. C12N 1/20; C12N 15/00; C12N 15/11

[52] U.S. Cl. ..................... 435/69.1; 435/440; 435/455; 435/471; 435/325; 435/252.3; 536/23.5

[58] Field of Search ........................... 536/23.5; 435/6, 435/172.3, 69.1, 325, 252.3, 252.33, 440, 455, 471

[56] References Cited

PUBLICATIONS

GenBank Accession No. R67292 Submitted by Hillier et al., The WashU–Merck EST Project; 30 May 1995.
GenBank Accession No. U51628 Submitted by J. Hoganesch; 1 Dec. 1996.

*Primary Examiner*—Paula K. Hutzell
*Assistant Examiner*—Patricia A. Duffy
*Attorney, Agent, or Firm*—Richard Aron Osman

[57] ABSTRACT

The invention provides methods and compositions relating to neuronal PAS domain proteins (NPAS) and related nucleic acids. The proteins may be produced recombinantly from transformed host cells from the disclosed NPAS encoding nucleic acids or purified from human cells. The invention provides isolated NPAS hybridization probes and primers capable of specifically hybridizing with the disclosed NPAS gene, NPAS-specific binding agents such as specific antibodies, and methods of making and using the subject compositions in diagnosis, therapy and in the biopharmaceutical industry.

4 Claims, No Drawings

NEURONAL BHLH-PAS DOMAIN PROTEINS

FIELD OF THE INVENTION

The field of this invention is transcription factor proteins involved in neuronal tissue.

BACKGROUND

Molecular biological studies reported during the past decade have identified a family of transcription factors designated basic helix-loop-helix (bHLH)-PAS proteins. Members of this protein family contain a conventional bHLH DNA binding domain located on the amino-terminal side of a PAS domain. PAS is an acronym derived from the initial three proteins observed to contain this polypeptide motif; the period gene product of fruit flies (1, 2, 3), the aryl hydrocarbon receptor nuclear transporter (4) and the single-minded gene product of flies (5). The PAS domain is roughly 260 amino acids in length and contains two direct repeats of roughly 60 amino acids (5).

Biochemical studies of the aryl hydrocarbon (AH) receptor have provided evidence that it is directly regulated by xenobiotic compounds (reviewed in 6). In its resting state the AH receptor is retained in the cytoplasm in association with heat shock protein 90 (HSP90) (7). Upon exposure to xenobiotic compounds, the AH receptor is released from HSP90 and dimerizes with the aryl hydrocarbon receptor nuclear transporter (ARNT), a second bHLH-PAS domain protein critical to the function of the AH receptor (4, 8). The activated AHR/ARNT heterodimer enters the nucleus and activates a battery of genes including those encoding P450 enzymes that facilitate detoxification (9, 10). The PAS domain of the AH receptor performs three biochemical functions in this regulatory pathway. In the latent state, the PAS domain binds HSP90 (7, 11). Upon activation, the PAS domain binds xenobiotic compounds, perhaps leading to release of HSP90 (7, 11, 12). Finally, upon association with ARNT, the PAS domain of each protein contributes a part of the dimer interface, thus facilitating formation of a DNA binding-competent transcription factor (13, 14).

Although other bHLH-PAS domain proteins have not been studied in equivalent biochemical detail, they have been implicated in an interesting and important spectrum of biological pathways. Hypoxia induced factor (HIF) and a related bHLH-PAS domain protein designated EPAS1 have been found to activate mammalian gene expression in response to hypoxia (15, 16). Both HIF and EPAS1 appear to function as obligate heterodimers with ARNT. HIF has been implicated in the activation of the gene encoding erythropoietin in hypoxic kidney tissue (17), whereas EPAS1 appears to control gene expression in vascular endothelial cells (16). The mechanisms by which HIF and EPAS1 are activated in response to hypoxia remain unresolved.

Two bHLH-PAS domain proteins, single-minded and trachealess, have been extensively studied in fruit flies. Recessive mutations in the gene encoding single-minded affect midline formation of the Drosophila melanogaster central nervous system (5, 18, 19). Loss of function mutations in the gene encoding trachealess impede tubulogenesis in the fly embryo (20, 21). Circadian rhythm in fruit flies is regulated by the product of the period gene, designated Per, which encodes a PAS domain protein devoid of a bHLH domain (1, 2, 5). Instead of acting in concert with another bHLH-PAS domain protein, Per interacts with the product of the timeless gene to synchronize fly behavior with the day/night cycle (22, 23, 24).

Recognizing that bHLH-PAS domain proteins regulate important biological processes in a variety of organisms, we set out to identify new members of this family of transcription factors. Here we provide the molecular characterization of neuronal PAS domain proteins (NPAS), exemplified by NPAS1 and NPAS2, including resolution of their primary amino acid sequences, assessment of their tissue distributions and temporal patterns of expression in mice, and the map locations of their encoding genes in mice and humans.

SUMMARY OF THE INVENTION

The invention provides methods and compositions relating to natural isolated neuronal PAS domain proteins (NPAS), related nucleic acids, and protein domains thereof having NPAS-specific activity. NPAS proteins can regulate the function of neurological tissue, such as brain tissue, etc. The proteins may be produced recombinantly from transformed host cells from the subject NPAS encoding nucleic acids or purified from mammalian cells. The invention provides isolated NPAS hybridization probes and primers capable of specifically hybridizing with the disclosed NPAS gene, NPAS-specific binding agents such as specific antibodies, and methods of making and using the subject compositions in diagnosis (e.g. genetic hybridization screens for NPAS transcripts), therapy (e.g. gene therapy to modulate NPAS gene expression) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequences of natural cDNAs encoding human and murine NPAS1 proteins are shown as SEQ ID NOS:1 and 2, respectively, and the full conceptual translates are shown as SEQ ID NOS:5 and 6, respectively. The nucleotide sequences of natural cDNAs encoding human and murine NPAS2 proteins are shown as SEQ ID NOS:3 and 4, respectively, and the full conceptual translates are shown as SEQ ID NOS:7 and 8, respectively. Human and murine-specific sequences are discerned by aligning the disclosed sequences. The NPAS proteins of the invention include incomplete translates of SEQ ID NOS: 1, 2, 3 and 4 and deletion mutants of SEQ ID NOS:5, 6, 7 and 8, which translates and deletion mutants have NPAS-specific amino acid sequence and binding specificity or function. Such active NPAS deletion mutants, NPAS peptides or protein domains comprise (i) at least 24, preferably at least about 26, more preferably at least about 30 consecutive residues of SEQ ID NO:5, 6, 7 or 8; (ii) at least 10, preferably at least about 12, more preferably at least about 14 consecutive residues of the bHLH regions of SEQ ID NO:5, 6, 7 or 8; or, at least 6, preferably at least about 8, more preferably at least about 10 consecutive residues of the PAS-B domains of SEQ ID NO:5, 6, 7 or 8. For examples, NPAS protein domains identified below are shown to provide dimerization, protein-binding, and nucleic acid binding function. Additional such domains are identified in and find use, inter alia, in solid-phase binding assays as described below.

NPAS-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an NPAS protein with a binding target is evaluated. The binding target may be a natural intracellular binding target such as another bHLH/PAS protein, a heat shock protein, or a nucleic acid sequence/binding site or other regulator that directly modulates NPAS activity or its localization; or non-natural binding target such a specific immune protein such as an antibody, or an NPAS specific agent such as those identified in screening assays such as described below. NPAS-binding specificity may assayed by binding equilibrium constants (usually at least about $10^7 M^{-1}$, preferably at least about $10^8 M^{-1}$, more preferably at least about $10^9 M^{-1}$), by the ability of the subject protein to function as negative mutants in NPAS-expressing cells, to elicit NPAS specific antibody in a heterologous host (e.g. a rodent or rabbit), etc. In any event, the NPAS binding specificity of the subject NPAS proteins necessarily distinguishes EPAS1, SIM1, SIM2, ARNT, AhR, TRH and HIF-1α proteins.

The claimed NPAS proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The NPAS proteins and protein domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides natural and non-natural NPAS-specific binding agents, methods of identifying and making such agents, and their use in diagnosis, therapy and pharmaceutical development. For example, NPAS-specific agents are useful in a variety of diagnostic and therapeutic applications. Novel NPAS-specific binding agents include NPAS-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. For diagnostic uses, the binding agents are frequently labeled, such as with fluorescent, radioactive, chemiluminescent, or other easily detectable molecules, either conjugated directly to the binding agent or conjugated to a probe specific for the binding agent. Agents of particular interest modulate NPAS function, e.g. NPAS-dependent transcriptional activation; for example, isolated cells, whole tissues, or individuals may be treated with an NPAS binding agent to activate, inhibit, or alter NPAS-dependent transcriptional processes.

The amino acid sequences of the disclosed NPAS proteins are used to back-translate NPAS protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural NPAS-encoding nucleic acid sequences (GCG software, Genetics Computer Group, Inc, Madison Wis.). NPAS-encoding nucleic acids used in NPAS-expression vectors and incorporated into recombinant host cells, e.g. for expression and screening, transgenic animals, e.g. for functional studies such as the efficacy of candidate drugs for disease associated with NPAS-modulated transcription, etc.

The invention also provides nucleic acid hybridization probes and replication/amplification primers having a NPAS cDNA specific sequence contained in SEQ ID NO:1, 2, 3 or 4 and sufficient to effect specific hybridization thereto (i.e. specifically hybridize with SEQ ID NO:1, 2, 3, or 4, respectively, in the presence of neuronal cell cDNA). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01M $NaPO_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. NPAS cDNA homologs can also be distinguished from other protein using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1, 2, 3, or 4 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of NPAS genes and gene transcripts and in detecting or amplifying nucleic acids encoding additional NPAS homologs and structural analogs. In diagnosis, NPAS hybridization probes find use in identifying wild-type and mutant NPAS alleles in clinical and laboratory samples. Mutant alleles are used to generate allele-specific oligonucleotide (ASO) probes for high-throughput clinical diagnoses. In therapy, therapeutic NPAS nucleic acids are used to modulate cellular expression or intracellular concentration or availability of active NPAS.

The invention provides efficient methods of identifying agents, compounds or lead compounds for agents active at the level of a NPAS modulatable cellular function. Generally, these screening methods involve assaying for compounds which modulate NPAS interaction with a natural NPAS binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an NPAS protein, which may be part of a fusion product with another peptide or polypeptide, e.g. a tag for detection or anchoring, etc. The assay mixtures comprise a natural intracellular NPAS binding target. While native binding targets may be used, it is frequently preferred to use portions (e.g. peptides) thereof so long as the portion provides binding affinity and avidity to the subject NPAS protein conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the NPAS protein specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the NPAS protein and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration, gel chromatography (e.g. gel filtration, affinity, etc.). For cell-based NPAS-dependent transcription assays, binding is detected by a change in the expression of an NPAS-dependent reporter, such as luciferase. Native NPAS DNA binding sites and NPAS-regulated genes are readily isolated by transforming cells with NPAS expression vectors and identifying up and down-regulated gene expression. Alternatively, high-specificity DNA-binding sites are readily produced by established methods involving binding to randomized oligonucleotides and repeatedly selecting and randomizing within highest affinity NPAS binders.

Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the NPAS protein to the target in the absence of the agent as compared with the binding affinity in the presence of the agent indicates that the agent modulates the binding of the NPAS protein to the NPAS binding target. Analogously, in the cell-based transcription assay also described below, a difference in the NPAS transcriptional induction in the presence and absence of an agent indicates the agent modulates NPAS-induced transcription. A difference, as used herein, is statistically significant and preferably represents at least a 50%, more preferably at least a 90% difference.

The following experimental section and examples are offered by way of illustration and not by way of limitation.

EXPERIMENTAL

Gene isolation and sequencing

The National Institute for Biological Information (NCBI) GenBank database was searched for expressed sequence tags (ESTs) bearing sequence similarity to the PAS domain of the aryl hydrocarbon receptor. ESTs designated #R67292 and #R58054 were identified and used to generate oligonucleotide primers for PCR amplification of hybridization probes. Mouse and human cDNA clones containing these two ESTs were obtained by hybridization probing of bacteriophage lambda cDNA libraries derived from mouse brain tissue, human brain tissue and HeLa cells. Individual clones were subjected to automated DNA sequencing allowing conceptual translation of the reading frames encoding NPAS1 and NPAS2. In-frame translation stop codons were observed 6 and 17 residues, respectively, upstream from the putative translation initiation codons of the human and mouse cDNA clones encoding NPAS1. An in frame stop codon was observed 39 residues upstream from the putative translation initiation codon of the mouse cDNA encoding NPAS2.

RNA blotting and in situ hybridization

Total RNA samples were purified from dissected mouse organs or staged mouse embryos using RNA-STAT (Tel-Test 'B') and subjected to electrophoresis on 1.2% agarose gels run in the presence of formaldehyde (25). Poly-A$^+$ RNA samples were purified from total RNA using mRNA purification reagents (Pharmacia) and subjected to the same analysis as for total RNA. Fractionated RNA was transferred to Nytran nitrocellulose filters (Schleicher & Schuell), cross-linked to the filter by ultraviolet light and probed by hybridization using Rapid-Hyb (Amersham) at 65° C. using $^{32}$P-labeled DNA derived from mouse cDNAs encoding either NPAS1 or NPAS2. Following hybridization, filters were washed at 65° C. in 0.1×SSC/0.1% SDS and exposed to X-ray film for 2–4 days.

The templates used to generate in situ RNA probes for NPAS1 and NPAS2 were cloned into a pGEM-T vector (Promega). For NPAS1, the probe corresponded to the cDNA sequence encoding amino acid residues 142–266. For NPAS2, the probe corresponded to the cDNA sequence encoding amino acid residues 92–234. Each labeling reaction utilized lug of linearized template, 50uCi of $^{35}$S-UTP (Amersham) and was transcribed using T7 RNA polymerase (Ambion). Incorporated $^{35}$S-UMP was separated from unincorporated nucleotides using a G50 spin column (Pharmacia). Both sense and anti-sense probes were utilized for in situ hybridization assays.

Mice (C57BL/6×SJL F1) at 11 days of age were anesthetized with metofane and perfused via the left ventricle with cold heparinized saline followed by cold 4% paraformaldehyde. The brain was dissected free of the skull and immersed in cold 4% paraformaldehyde overnight at 4° C. The tissue was placed in 70% ethanol, dehydrated through graded alcohols, cleared in xylene and infused with paraffin. Coronal and parasagittal sections of the brain were cut at 4 um intervals and mounted on Vectabond treated slides (Vector Laboratories). Contiguous sections were probed with sense or anti-sense transcripts of NPAS1 or NPAS2, or stained for Nissl granules to identify individual neurons.

in situ hybridization was performed to determine the cellular and regional expression patterns of the Npas1 and Npas2 genes in the mouse brain. Paraffin was removed from the sections with xylene, followed by graded ethanol hydration, post-fixation in 4% paraformaldehyde, pronase digestion (20 ug/ml pronase for 7.5 min), and acetylation (0.1M triethanolamine-HCL, pH 7.5, 0.25% acetic anhydride for 5 min). Hybridization was conducted for 12 hr at 55° C. in a solution containing 50% formamide, 0.3% dextran sulfate, 1×Denhardt's solution, 0.5mg/ml tRNA and 7.5 ×10$^6$ cpm/ml riboprobe. Following hybridization the slides were washed in 5×SSC at 55° C. for 40 min followed by a wash in high stringency buffer (50% formamide, 2×SSC supplemented by 10 mM dithiothreitol) at 65° C. for 30 min. A coat of K.5 nuclear emulsion (Ilford) was applied to the slides before exposure at 4° C. for 21 (NPAS2) or 28 (NPAS1) days. The emulsion was developed, sections were counterstained with hematoxylin, and examined using bright- and dark-field optics.

Genetic mapping

The human NPAS1 and NPAS2 genes were localized to specific chromosomes using a panel of 17 human×Chinese hamster hybrid cell lines (26). The murine Npas1 and Npas2 genes were mapped by analyzing a panel of 16 mouse× Chinese hamster and 2 mouse×rat somatic cell hybrid lines (27). Polymerase chain reaction (PCR) primers used to amplify human NPAS2, murine Npas1 and murine Npas2 sequences were derived from the 3' untranslated region. PCR primers for human NPAS1 were derived from its coding region. PCR conditions were 94° C., 3 min; then 35 cycles of 94° C., 30 sec; 55° C., 30 sec; 72° C., 60 sec; followed by 72° C., 7 min. expected PCR products were obtained from total human or mouse genomic DNA, but not from hamster or rat DNA.

DNA of the interspecies mapping panel, BSS panel 2, was obtained from the Jackson Laboratory (28). Parental strains of C57BL/6JEi (B6) and *M. spretus* (SPRET/Ei) were screened for DNA variants by PCR amplification and single-stranded conformation analysis (SSCA). To distinguish the PCR products from amplification of these two DNA samples, SSCA was carried out (29). The DNA was denatured by mixing 2 ul of PCR product with 10 ul of 90% formamide, 20 mM EDTA and incubated at 95° C. for 5 min, followed by cooling on ice. The mix was loaded onto a nondenaturing 12% polyacrylamide gel containing 1×TBE. Electrophoresis was performed in a Tris-glycine buffer at 200V for 3 hr at 4° C. DNA fragments were visualized by silver staining. The PCR primers for amplifying mouse Npas2 were the same as those used for SCH mapping. PCR primers for amplifying mouse Npas1 were from exonic sequences. Amplification with both sets of PCR primers allowed detection of strain-specific variation between parental strains (C57BL/6JEi vs SPRET/Ei). All 94 DNA samples from the BSS panel 2 were typed and scored. The mouse Npas1 and Npas2 distribution patterns were sent to the Jackson Laboratory backcross service for comparison to the existing typing database.

Two human radiation hybrid mapping panels, GeneBridge 4 (Whitehead Genome Center) and Stanford G3 (Stanford Genome Center) were used to further define the localization of the human NPAS1 and NPAS2 genes. Typing was carried out using primers and PCR conditions described above. The maximum likelihood analysis results were obtained by submitting the raw scores to rhserver@shgc.stanford.edu and http://www-genome.wi.mit.edu/cgibin/contig/rhmapper.pl.

Identification of two new bHLH-PAS domain proteins

Clones corresponding to two expressed sequence tags (ESTs) found in the GenBank data base were recovered from mouse and human cDNA libraries. Conceptual translation of both ESTs, designated #R67292 and #R58054, revealed primary amino acid sequences related to the PAS domain of the aryl hydrocarbon receptor. cDNAs corresponding to EST#67292 are hereafter designated NPAS1, whereas cDNAs corresponding to EST#R58054 are designated NPAS2. Multiple cDNAs encoding the mouse and human versions of NPAS1 and NPAS2 were isolated and subjected to automated sequencing. SEQ ID NOS: 5 and 7 show the conceptually translated amino acid sequences of human and mouse NPAS1. SEQ ID NOS: 6 and 8 show the sequences of human and mouse NPAS2.

The mouse and human NPAS1 proteins share 86% identity at the level of primary amino acid sequence and specify, respectively, polypeptides of 63.7 kDa and 62.7 kDa. The mouse and human NPAS2 proteins share 87% identity at the level of primary amino acid sequence and specify polypeptides of 90.9 kDa and 91.8 kDa. Having observed amino acid sequence similarity between NPAS1, NPAS2 and established bHLH-PAS proteins, we identify these as new members of this family of transcription factors. Several features of their primary amino acid sequences support their identification as members of the bHLH-PAS domain family.

Each of the functionally defined regions of the bHLH-PAS domain rely on defined arrangements of amino acids to specify function. In an alignment of the bHLH domains of nine members of the bHLH-PAS domain family of proteins (4, 15, 16, 20, 21, 30, 31), eighteen residues were observed to be conserved within the bHLH domain of at least seven of the nine proteins analyzed. The bHLH domain of NPAS1 contained the consensus amino acid at seventeen of these eighteen positions. The bHLH domain of NPAS2 appeared to diverge from the bHLH consensus more substantially than NPAS1. NPAS2 contained the consensus amino acid at only nine of the eighteen positions. NPAS2 likewise appeared to be missing three residues in the loop region separating helix 1 from helix 2. Given, however, that loop size is known to vary among other bHLH proteins (reviewed in 32), and that the majority of NPAS2s variant amino acids represent conservative changes, it likely specifies a functional bHLH domain.

In an alignment of the two PAS domains of the same set of bHLH-PAS domain proteins, the PAS-A domain was observed to contain eighteen residues conserved among at least seven of the nine proteins analyzed. The putative PAS-A domain of NPAS1 contained conserved amino acids at sixteen of these eighteen positions, whereas that of NPAS2 contained identities at twelve of the most highly conserved residues. Similar analysis of the PAS-B domains revealed twelve highly conserved residues, eight of which were found in NPAS1 and eleven in NPAS2. The conservation of these signature amino acid residues in the putative bHLH, PAS-A and PAS-B domains of NPAS1 and NPAS2 favor the interpretation that these protein represents a functional member of bHLH-PAS family of transcriptional regulatory proteins. NPAS1 and NPAS2 mRNAs are enriched in neuronal tissues:

The distribution of mouse tissues that express NPAS1 and NPAS2 mRNAs was evaluated by RNA blotting. Seventeen tissues were dissected from adult mice and evaluated for NPAS1 mRNA abundance. Brain and spinal cord tissues contained a 2.4 kb RNA that hybridized to the NPAS1 cDNA probe, whereas the remaining fifteen tissues failed to show a detectable hybridization signal. Ethidium bromide staining revealed that each RNA sample was grossly intact, indicating that NPAS1 mRNA is significantly enriched in neuronal tissues. NPAS2 mRNA abundance was evaluated in sixteen tissues dissected from adult mice, including fourteen that were tested for NPAS1 mRNA abundance and two additional tissues (colon and pancreas). The highest level of the 2.6 kb NPAS2 mRNA was observed in brain tissue. Less substantive hybridization was observed in spinal cord, small intestine, uterus and colon. Although the tissue distribution of NPAS2 mRNA was less selectively restricted to neuronal tissue than that of NPAS1, ethidium bromide staining of RNA samples showed relative consistencies in both abundance and integrity of 18S and 28S ribosomal RNA. Thus, relative to these structural RNAs, NPAS2 mRNA was found to be more enriched in brain than any of the sixteen other tissues that were tested.

Developmental appearance of NPAS1 and NPAS2 mRNAs

The temporal appearance of NPAS1 and NPAS2 mRNA was examined by RNA blotting using samples obtained from mouse embryos and early post-natal animals. Embryos were obtained from timed matings of NIH Swiss strain animals. Embryos staged between embryonic day 10 (E10) and 13 (E13) were dissected to retrieve the anterior ⅓ of the embryonic mass. Later staged embryos and post-natal animals were dissected to isolate the brain from other tissues.

NPAS1 mRNA was detected on blots prepared using total RNA. NPAS-1 mRNA was first observed between embryonic day 15 and 16. Its relative abundance appeared to increase during late embryogenesis and be maintained during post-natal development. The enrichment of NPAS1 mRNA at post-natal day 3 (P3) is partially offset by a slight, relative increase in the amount of total RNA that was present in that particular sample.

NPAS2 mRNA was detected on blots prepared using poly-A$^+$ RNA from late stage mouse embryos, post-natal animals and adults. In all cases, brain tissue was dissected and retrieved for RNA isolation. NPAS2 mRNA was first observed three days post-birth. The apparent abundance of NPAS2 mRNA increased slightly through post-natal day 9, yet was substantially elevated in brain tissue obtained from adult mice. As a control for RNA integrity and loading, the same filter that was used for detection of NPAS2 mRNA was stripped and blotted using a cDNA probe specific to β-actin.

in situ expression patterns of NPAS1 and NPAS2 mRNA

Brain tissue was dissected following anesthetization and perfusion of 11 day old mice. Following immersion fixation the material was embedded in paraffin, sectioned and applied to glass microscope slides. Sense and anti-sense probes specific to the mouse genes encoding NPAS1 and NPAS2 were employed under standard conditions of in situ hybridization. Both NPAS1 and NPAS2 mRNA expression was restricted to large, cytoplasm-rich neurons having pale-staining nuclei and prominent nucleoli. Their identity was confirmed as neurons by cresyl echt violet staining for Nissl substance on contiguous sections.

The overall distributions of NPAS1 and NPAS2 mRNA in the mouse brain appeared to be broad, complex and largely non-overlapping. In general, the NPAS1 hybridization signal tended to be more discrete and intense than that of NPAS2, whereas the NPAS2 hybridization probe appeared to stain a higher proportion of neurons than NPAS1.

NPAS1 expression in the neocortex was observed in deep pyramidal cell layers, whereas only rare neurons in the superficial layers were positive. Small numbers of intensely expressing neurons were observed in the polymorph layer of the hippocampus and dentate gyrus. In the basal ganglia, expression was restricted to the amygdala complex. NPAS1 mRNA also appeared in the ventroposterior area of the thalamus as well as in neurons in the medial nuclei of the hypothalmus. In the mesencephalon, the intermediate grey area of the superior colliculus was positive, as was the sensory trigeminal nucleus of the pons. No expression of NPAS1 was observed in the cerebellum, caudoputamen or inferior colliculus.

The distribution of NPAS2 mRNA detected by in situ hybridization ranged broadly throughout all layers of the neocortex with the exception of layer I. The signal extended into the subiculum and the pyramidal neurons of the CA1 area of the hippocampus. Small numbers of neurons in the superficial aspect of the pyramidal layer of the inner and outer blades of the dentate gyrus also appeared to express NPAS2 mRNA. More abundant numbers of neurons diffusely distributed throughout the caudoputamen and pallidum of the basal ganglia were NPAS2 positive, as were nuclei of the anteriolateral thalamus. No signal was observed in the medulla, pons, superior or inferior colliculi, cerebellum or olfactory bulbs.

Chromosomal map locations of the genes encoding NPAS1 and NPAS2

Somatic cell hybrids were utilized to assign the human NPAS1 gene to chromosome 19, mouse Npas1 to chromosome 7, human NPAS2 to chromosome 2, and mouse Npas2 to chromosome 1. A regional mapping panel for human chromosome 2 was typed by NPAS2 specific primers which placed the NPAS2 gene in region 2q13–q33.

Mouse backcross mapping panels were employed to more closely define the locations of the genes encoding NPAS1 and NPAS2. DNA from the BSS panel 2 (Jackson Laboratory) was typed by PCR-SSCA analysis using primers specific to the mouse Npas1 and Npas2 genes. The Npas1 gene fit a proximal chromosome 7 map position in a large cluster of non-recombining loci that included D7Mit56, D7Mit75 and D7Bir6. Thus, the Npas1 gene was placed on the linkage map of mouse chromosome 7 around 2 cM from the centromere. The Npas2 gene was found to be closely linked to two markers, D1Bir8 and D1Hun 31, on chromosome 1. It was mapped between these two markers with one recombination occurring between Npas2 and each marker. Thus, the Npas2 gene was placed on the linkage map of mouse chromosome 1 between 21 and 22 cM from the centromere.

To further define the location of the human NPAS1 gene, two radiation hybrid (RH) mapping panels were typed by PCR amplification using NPAS1 specific primers. In the Stanford G3 RH mapping panel, 12 of the 83 RH cell lines were positive for the human-specific NPAS1 gene signal. By maximum likelihood analysis, the NPAS1 gene was found to be closely linked to STS markers D19S851, D19S985, D19S995, D19S1000, D19S1096, D19S412 and D19S1105. These markers are clustered as chromosome 19 Bin #23 in the Stanford Genome Center (SGC) RH map (http://shgc-www.stanford.edu/RHmap.html). In the GeneBridge 4 mapping panel, 23 of 93 RH cell lines were positive for the human-specific NPAS1 gene signal. By maximum likelihood analysis, NPAS1 was placed 0.9 centiRays (cR3000) from the chromosome 19 marker WI-9028. The order for placement of NPAS1 was D19S408—WI-9028—NPAS1—D19S412. Since D19S408 and D19S412 were respectively mapped to 19q13.2 and 19q13.3, NPAS1 is most likely located at 19q13.2–q13.3.

Two RH mapping panels were used to further define the location of the human NPAS2 gene on chromosome 2. In the G3 RH mapping panel, 23 of 83 RH cell lines were positive for the human-specific NPAS2 gene signal. By maximum likelihood analysis, NPAS2 was found to be closely linked to STS markers D2S2886, D2S2776, D2S2311 and D2S2187, which are clustered as chromosome 2 Bin #44 and

45 in the SGC RH map. In the GeneBridge 4 mapping panel, 33 of the 93 RH lines were positive and NPAS2 was placed 6.2 centiRays (cR3000) from the chromosome 2 marker D2S373. D2S2311, D2S2187 and D2S373 are known markers in the WC2.8 contig (Whitehead Institute/ MIT Center for Genome Research). Thus, the NPAS2 gene is likely present in this yeast artificial chromosome contig. Since there is no cytogenetic localization of the known STS markers and genes in WC2.8 or of chromosome 2 Bin #44 and #45, more distantly located flanking markers were examined. According to Bray-Ward et al. (33), the marker D2S139 (WC2.5) maps to 2p11.2–12. The marker D2S135 (WC2.9) was mapped to 2q11.2–12, D2S160 (WC2.9) to 2q12–13, and D2S114 (WC2.11) to 2q21–22. Since the RH data placed the NPAS2 gene at 2p11.2–2q13, while the somatic cell hybrid data suggest 2q13–q33, we conclude that the map location for this gene is chromosome 2 band q 13.

Examination of the mouse genome surrounding the Npas1 locus revealed two neurological mutant loci, nv and Ind, close to Npas1. nv, Nijmegen waltzer, is a recessive mutation that has been mapped around 0–4.2 cM of chromosome 7 (34). Homozygous nv animals show circling behavior, head shaking and hearing defects. Ind, lumbosacral neuroaxonal dystrophy, is recessive and has been mapped around 2 cM of chromosome 7 (35). Ind homozygous animals have dystrophic axons in the low lumbar and sacral spinal cord levels. Mutants can be identified by 3 weeks of age by a slight tremor of the head. They later develop wobbly gait, mild head tremors, nervous behavior and a tendency to drag their hind limbs. It will be of special interest to determine whether the Npas1 gene is disrupted in either of these mouse mutants.

REFERENCES

1. Jackson, F. R., Bargiello, T. A., Yun, S.-H., & Young, M. W. (1986) *Nature* 320, 185–188.
2. Citri, Y., et al. (1987) *Nature* 326, 42–47.
3. Huang, Z. J., Edery, I., & Rosbash, M. (1993) *Nature* 364, 259–262.
4. Hoffman, E. C., et al. (1991) *Science* 252, 954–958.
5. Nambu, J. R., Lewis, J. O., Wharton, K. A., Jr., & Crews, S. T. (1991) *Cell* 67, 1157–1167.
6. Hankinson, O. (1995) *Annu. Rev. Pharmacol. Toxicol.* 35, 307–340.
7. Antonsson, C., et al. (1995) *Mol. Cell. Biol.* 15, 756–765.
8. Reisz-Porszasz, S., et al. (1994) *Mol. Cell. Biol.* 14, 6075–6086.
9. Whitlock, J. P., Jr., et al. (1996) *FASEB J.* 10, 809–818.
10. McLane, K. E. & Whitlock, J. P., Jr. (1994) *Receptor* 4, 209–222.
11. Coumailleau, P., et al. (1995) *J. Biol. Chem.* 270, 25291–25300.
12. Fukunaga, B. N., et al. (1995) *J. Biol. Chem.* 270, 29270–29278.
13. Whitelaw, M. L., Gustafsson, J.-A., & Poellinger, L. (1994) *Mol. Cell. Biol.* 14, 8343–8355.
14. Lindebro, M. C., Poellinger, L., & Whitelaw, M. L. (1995) *EMBO J.* 14, 3528–3539.
15. Wang, G. L., et al. (1995) *Proc. Natl. Acad. Sci. USA* 92, 5510–5514.
16. Tian, H., McKnight, S. L., & Russell, D. W. (1996) submitted.
17. Wang, G. L., & Semenza, G. L. (1993) *Blood* 82, 3610–3615.
18. Crews, S. T., Thomas, J. B., & Goodman, C. S. (1988) *Cell* 52, 143–151.
19. Nambu, J. R., Franks, R. G., Hu, S., & Crews, S. T. (1990) *Cell* 63, 63–75.
20. Isaac, D. D., & Andrew, D. J. (1996) *Genes & Dev.* 10, 103–117.
21. Wilk, R., Weizman, I., & Shilo, B.-Z. (1996) *Genes & Dev.* 10, 93–102.
22. Hunter-Ensor, M., Ousley, A., & Sehgal, A. (1996) *Cell* 84, 677–685.
23. Zeng, H., Qian, Z., Myers, M. P., & Rosbash, M. (1996) *Nature* 380, 129–135.
24. Myers, M. P., et al. (1996) *Science* 271, 1736–1740.
25. Sambrook, J., et al. (1989) *Molecular Cloning* (2nd ed) (CSHL Press), pp. 7.43–7.45.
26. Francke, U., et al. (1986) *Cold Spring Harbor Symp. Quant. Biol.* 51, 855–866.
27. Li, X., Yin, X., Perez-Jurad, L., Bonadio, J., & Francke, U. (1995) *Mamm. Genome* 6, 42–45.
28. Rowe, L. B., et al. (1994) *Mamm. Genome* 5, 253–274.
29. Sugano, K., et al. (1993) *Methods Lab. Investt.* 65, 361–366.
30. Fan, C.-M., et al. (1996) *Mol. Cell. Neurosci.* 7, 1–16.
31. Dolwick, K. M., et al. (1993) *Mol. Pharmacol.* 44, 911–917.
32. Lassar, A. B., & Weintraub, H. (1992) in *Transcriptional Regulation*, eds. McKnight, S. L. & Yamamoto, K. R. (Cold Spring Harbor Laboratory Press), pp. 1037–1062.
33. Bray-Ward, P., et al. (1996) *Genomics* 32, 1–14.
34. van Abeelen, J. H., & van der Kroon, P. H. W. (1967) *Genet. Res.* 10, 117–118.
35. Bronson, R. T., Sweet, H. O., Spencer, C. A., & Davisson, M. T. (1992) *J. Neurogenet.* 8, 71–83.

EXAMPLES

1. Protocol for high throughput NPAS1-HSP90 heterodimer formation assay.

A. Reagents:

Neutralite Avidin: 20 $\mu$g/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM P-mercaptoethanol, 1 mg/ml BSA, cocktail of protease inhibitors.

$^{33}$P NPAS1 protein 10×stock: $10^{-8}$–$10^{-6}$M "cold" NPAS1 supplemented with 200,000–250,000 cpm of labeled NPAS1 (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2mM $NaVo_3$ (Sigma #S-6508) in 10 ml of PBS.

HSP90: $10^{-7}$–$10^{-5}$M biotinylated HSP90 in PBS.

B. Preparation of assay plates:

Coat with 120 $\mu$l of stock N-Avidin per well overnight at 4° C.

Wash 2 times with 200 $\mu$l PBS.

Block with 150 $\mu$l of blocking buffer.

Wash 2 times with 200 $\mu$l PBS.

C. Assay:

Add 40 $\mu$l assay buffer/well.

Add 10 $\mu$l compound or extract.

Add 10 $\mu$l $^{33}$P-NPAS1 (20–25,000 cpm/0.1–10 pmoles/well=$10^{-9}$–$10^{-7}$M final conc).

Shake at 25° C. for 15 minutes.

Incubate additional 45 minutes at 25° C.

Add 40 $\mu$M biotinylated HSP90 (0.1–10 pmoles/40 ul in assay buffer)

Incubate 1 hour at room temperature.
Stop the reaction by washing 4 times with 200 μM PBS.
Add 150 μM scintillation cocktail.
Count in Topcount.
D. Controls for all assays (located on each plate):
 a. Non-specific binding
 b. Soluble (non-biotinylated HSP90) at 80% inhibition.
2. Protocol for high throughput human NPAS2/ARNT- DNA complex formation assay.
 A. Reagents:
 Neutralite Avidin: 20 μg/ml in PBS.
 Blocking buffer: 5% BSA, 0.5% Tween 20 in PBS; 1 hour at room temperature.
 Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.
 $^{33}$P human NPAS2 protein 10×stock: $10^{-8}$–$10^{-6}$M "cold" human NPAS2 supplemented with 200,000–250,000 cpm of labeled human NPAS2 (Beckman counter). Place in the 4° C. microfridge during screening.
 Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2mM NaVo$_3$ (Sigma #S-6508) in 10 ml of
 DNA: $10^{-7}$–$10^{-4}$M biotinylated DNA comprising NPAS2 recognition sequence in PBS.
 ARNT protein: $10^{-7}$–$10^{-5}$M ARNT in PBS.
 B. Preparation of assay plates:
 Coat with 120 μM of stock N-Avidin per well overnight at 4° C.
 Wash 2 times with 200 μM PBS.
 Block with 150 μM of blocking buffer.
 Wash 2 times with 200 μM PBS.
 C. Assay:
 Add 40 μM assay buffer/well.
 Add 10 μM compound or extract.
 Add 10 μM $^{33}$P-h NPAS2 protein (20–25,000 cpm/0.1–10 pmoles/well=$10^{-9}$–$10^{-7}$M final).
 Add 10 μl ARNT protein.
 Shake at 25° C. for 15 minutes.
 Incubate additional 45 minutes at 25° C.
 Add 40 μM biotinylated DNA (0.1–10 pmoles/40 ul in assay buffer)
 Incubate 1 hour at room temperature.
 Stop the reaction by washing 4 times with 200 μM PBS.
 Add 150 μM scintillation cocktail.
 Count in Topcount.
 D. Controls for all assays (located on each plate):
 a. Non-specific binding
 b. Soluble (non-biotinylated NPAS2/ARNT combination) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2078 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
GAATTCCCAG  CCCGCGCGTC  CCGCTGCGCC  CCGCGCGCCC  CGGGGTCTAT  GGAGCTGCCC        60

CTCCGCGCCG  CCCGGCCGGC  CCCACGCCGC  GCCCGGAGCG  TGCTCTGCGG  CCAAGTAATC       120

GGACTGGCGG  TCCTGCGGGA  GACTCGGGGC  TCGGAGCCCG  CCTGAGCGAG  CCCCCCGGAG       180

ATGGCGGCCC  CCTATCCCGG  CAGTGGCGGC  GGAAGCGAGG  TCAAATGCGT  GGGAGGCCGC       240

GGCGCCAGCG  TCCCCTGGGA  CTTTCTACCC  GGGCTGATGG  TCAAGGCGCC  GTCCGGACCG       300

TGCCTGCAGG  CGCAGCGCAA  GGAGAAGTCC  CGGAACGCGG  CGCGCTCGCG  GCGCGGGAAG       360

GAGAACCTGG  AGTTCTTCGA  GCTGGCCAAG  CTTCTCCCGC  TGCCCGGCGC  CATCTCCATC       420

CAGCTGGACA  AGGCTTCCAT  CGTGCGCCTC  AGCGTCACCT  ACCTCCGCCT  GCGCCGGTTC       480
```

-continued

| | | | | | | |
|---|---|---|---|---|---|---|
| GCCGCGCTGG | GGGCGCCGCC | CTGGGGGCTG | AGAGCCGCGG | GGCCGCCAGC | TGGCCTCGCC | 540 |
| CCAGGCCGCC | GCGGCCCCGC | AGCGCTGGTC | TCCGAAGTCT | TCGAGCAGCA | CCTGGGAGGT | 600 |
| CACATCTTGC | AGTCCCTGGA | TGGCTTTGTG | TTCGCCTTGA | ACCAGGAAGG | AAAATTCCTC | 660 |
| TACATCTCAG | AGACAGTCTC | CATCTATCTG | GGTCTCTCAC | AGGTGGAGAT | GACGGGCAGC | 720 |
| AGCGTCTTCG | ACTACATTCA | CCCTGGGGAC | CACTCAGAGG | TGCTGGAGCA | ACTGGGGCTG | 780 |
| CGGACGACGA | CGCCCGGCCC | CCCAACCCCG | TCCTCCGTCT | CCTCTTCCTC | CTCCTCTTCC | 840 |
| TCTTCGCTTG | CAGATACCCC | CGAGATCGAG | GCCAGCCTCA | CCAAGGTGCC | CCCCTCCTCC | 900 |
| CTGGTCCAGG | AGCGCTCCTT | CTTTGTCCGC | ATGAAATCCA | CGCTCACCAA | GAGGGGGCTG | 960 |
| CACGTCAAGG | CCTCAGGGTA | CAAGGTCATC | CACGTGACTG | GGCGCCTTCG | GGCCCACGCC | 1020 |
| CTGGGCCTTG | TGGCCCTCGG | GCACACGTTG | CCCCCGGCCC | CCTGGCTGA | GCTGCCACTC | 1080 |
| CATGGACACA | TGATCGTCTT | CCGTCTCAGC | CTGGGTCTCA | CCATCCTTGC | TTGTGAGAGC | 1140 |
| AGAGTCAGCG | ACCACATGGA | CCTGGGGCCC | TCAGAGCTGG | TGGGCCGCAG | CTGCTACCAG | 1200 |
| TTTGTCCACG | GACAAGACGC | CACGAGGATC | CGCCAGAGCC | ACGTGGACTT | GCTGGACAAG | 1260 |
| GGTCAGGTGA | TGACTGGTTA | CTACCGTTGG | CTGCAGCGTG | CCGGGGGCTT | CGTGTGGCTG | 1320 |
| CAGTCTGTGG | CCACAGTGGC | TGGGAGCGGG | AAGAGCCCCG | GGAGCACCA | TGTGCTTTGG | 1380 |
| GTCAGCCACG | TGCTCAGCCA | AGCCGAGGGT | GGCCAAACTC | CTTTGGATGC | CTTCCAGCTT | 1440 |
| CCAGCCAGCG | TGGCCTGTGA | GGAGGCATCC | AGCCCGGGGC | CAGAGCCCAC | AGAGCCGGAG | 1500 |
| CCTCCGACGG | AAGGGAAGCA | GGCTGTCCCA | GCGGAGAACG | AGGCCCCCA | GACCCAGGGC | 1560 |
| AAACGCATCA | AAGTGGAGCC | CGGCCCGAGG | GAAACCAAAG | GTTCCGAGGA | CAGTGGCGAC | 1620 |
| GAGGATCCCT | CCAGCCACCC | GGCCACACCG | AGGCCCGAGT | TCACCTCTGT | CATCCGGGCA | 1680 |
| GGGGTCCTGA | AGCAGGATCC | GGTGCGGCCA | TGGGGCCTGG | CGCCTCCCGG | GGACCCCCCG | 1740 |
| CCCACCCTCC | TGCACGCGGG | CTTCCTGCCG | CCGGTGGTGC | GGGGCCTGTG | CACACCCGGC | 1800 |
| ACCATCCGCT | ACGGCCCCGC | GGAGCTGGGC | CTGGTGTACC | CGCACCTGCA | GAGGCTGGGT | 1860 |
| CCGGGCCCCG | CGCTCCCGGA | GGCCTTTTAC | CCGCCCCTGG | GCCTGCCCTA | CCCGGGGCCC | 1920 |
| GCGGGCACCA | GGCTGCCGCG | GAAGGGGGAC | TGAGGACTGG | CAGAGCTGCC | GGCGCCGGAC | 1980 |
| CCTGCGACAA | CCGGGGTCCC | CCAGGACAGT | AGGCCCGGCT | CTGCCCGTAG | CCCTGAGAAT | 2040 |
| TAAACGCCGG | CTCTCCCTGC | AAAAAAAAAA | AAAAAAA | | | 2078 |

( 2 ) INFORMATION FOR SEQ ID NO:2:

( i ) SEQUENCE CHARACTERISTICS:
        ( A ) LENGTH: 2082 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| CCAGGGAACT | GAGCCCCACC | TGCGACTCCT | TCGCACCTGA | ATTCCCGAGT | CCCCGTCGAG | 60 |
| ATGGCGACCC | CCTATCCCAG | AAGCGGTGGC | CGAGGTGAAG | TCAAGTGCGG | GGGCGGCCGT | 120 |
| GGAGCCGGCG | TCCCCTGGGA | TTTCCTGCCT | GGGCTGATGG | TCAAGGCCCC | GCCCGGACCC | 180 |
| TGCCTGCAGG | CGCAGCGCAA | AGAGAAGTCC | CGCAACGCTG | CGCGCTGGCG | ACGCGGGAAG | 240 |
| GAAAATCTGG | AGTTCTTCGA | GCTAGCCAAG | CTGCTCCCTC | TGCCCGGTGC | CATCTCCAGC | 300 |
| CAGCTGGACA | AGGCGTCCAT | CGTGCGTCTT | AGCGTCACCT | ACCTCCGCCT | GCGTCGTTTT | 360 |
| GCCGCGCTGG | GGGCGCCGCC | CTGGGGGTTG | CGGGCCGTCG | GGCCTCCGGC | TGGCCTCGCC | 420 |

-continued

| | | | | | | |
|---|---|---|---|---|---|---|
| CCAGGCCGCC | GAGGCCCTGT | GGCTCTGGTC | TCTGAAGTCT | TCGAGCAACA | CCTAGGTGGA | 480 |
| CACATCCTAC | AGTCCTTGGA | TGGCTTCGTG | TTCGCTTTGA | ACCAGGAAGG | GAAATTTCTC | 540 |
| TACATCTCAG | AGACAGTGTC | CATCTACCTG | GGTCTCTCAC | AGGTGGAGCT | GACGGGCAGC | 600 |
| AGCGTCTTCG | ACTACATCCA | TCCTGGGGAC | CACTCGGAGG | TCCTAGAGCA | ACTTGGATTG | 660 |
| CGGGCTGCAA | GCATCGGTCC | CCCTACACCA | CCTTCCGTGT | CCTCCTCTTC | CTCATCGTCT | 720 |
| TCCTCCTCGC | TGGTGGACAC | CCCTGAGATT | GAAGCCAGCC | CCACCGAGGC | ATCGCCTGCC | 780 |
| TTCCGAGCCC | AAGAGCGGTC | CTTCTTTGTC | CGCATGAAGT | CCACCCTCAC | CAAGAGGGGC | 840 |
| CTGAATGTCA | AAGCCTCGGG | GTACAAGGTC | ATTCATGTGA | CAGGGCGCCT | GAGGGCCCGA | 900 |
| GCCCTGGGTC | TTGTAGCCCT | TGGACACACG | CTGCCCCAG | CCCCACTGGC | TGAGCTGCCT | 960 |
| TTGCACGGAC | ACATGATTGT | CTTCCGCCTC | AGCCTGGGCC | TCACCATCCT | TGCTTGTGAG | 1020 |
| AGCAGAGTTA | GCGACCATAT | GGACATGGGG | CCCTCAGAGC | TTGTGGGACG | CAGCTGCTAC | 1080 |
| CAGTTTGTTC | ATGGACAGGA | TGCAACCAGG | ATCCGCCAAA | GCCATCTGGA | CCTGCTGGAC | 1140 |
| AAAGGGCAGG | TGGTGACTGG | TTACTACCGT | TGGCTGCAGC | GTGCGGGGGG | CTTCGTGTGG | 1200 |
| CTGCAGTCTG | TAGCCACTGT | GGCCGGGAAC | GGGAAGAGCA | CTGGGGAGCA | TCACGTGCTG | 1260 |
| TGGGTCAGTC | ACGTGCTCAG | CAATGCTGAA | GGTAGTCAAA | CACCCCTGGA | TGCCTTCCAG | 1320 |
| CTTCCAGCTA | TTGTGTCTCA | GGAGGAGCCA | TCCAGGCCAG | GCCCAGAGCC | CACAGAGGAA | 1380 |
| GAGCCTCCAG | TTGACGGGAA | GCAGGCTGTG | CCTGCGGACC | AGGACAAGGA | CAAGGACCCT | 1440 |
| CAGGCCCGAG | GCAAACGCAT | CAAAGTGGAG | GCCAGCCCGA | AGGAAGCTAG | AGGCTCAGAG | 1500 |
| GACAGTGGAG | AAGAGGAGCT | CTCGGATCCA | CCGGCTCCAC | CTCGGCCAGA | ATTCACTTCT | 1560 |
| GTCATCCGGG | CGGGAGCCCT | GAAGCATGAT | CCAGTGCTGC | CGTGGGGCTT | GACAACTCCC | 1620 |
| GGAGACCCCT | CACCCGCCCT | CCTTCATGCA | GGCTTCCTGC | CACCCGTTGT | GCGGGGCCTG | 1680 |
| TGCACCCCAG | GCACCATCCG | CTATGGCCCT | GCGGAGTTGA | GCCTGATGTA | TCCACATCTG | 1740 |
| CACAGGCTGG | GCGCAGGCCC | CTCGCTTCCA | GAGGCCTTTT | ACCCTACGCT | GGGCTTGCCC | 1800 |
| TATCCGGGGC | CCACAGGTAC | TAGGGTGCAG | CGGAAGGGAG | ACTGAAGACA | GTGTAACACC | 1860 |
| AGAGGGCCAA | ACCTGAGACA | CAGATCAAGT | CCTGGAGTCA | TTCTTGAGAA | TTAAACACCA | 1920 |
| TGCCCTAAGG | GGCTCCCTCC | CCGGGGGATG | CTGCCTCTCA | AAAAAAAAA | AAAAAAAAA | 1980 |
| AAAAAAAAA | AAAAAAAAA | AAAAAAAAA | AAAAAAAAA | AAAAAAAAA | AAAAAAAAA | 2040 |
| AAAAAAAAA | AAAAAAAAA | AAAAAAAAA | AAAAAAAAA | AA | | 2082 |

( 2 ) INFORMATION FOR SEQ ID NO:3:

( i ) SEQUENCE CHARACTERISTICS:
        ( A ) LENGTH: 4010 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| GTTTGCCGCG | CGAGCAGCCG | GCCTCTCGCA | GGAGCCGAGG | GACCCGCGCG | GCTGCGGCCC | 60 |
| AGGAGCGGCG | GCCGCGGAGC | CCGGAGACCC | GCAGCCGCGG | CGGCGGCGGC | GGCGGCGGCA | 120 |
| GCAGCTAGAG | CAGCGCCTCC | CGCCGCCGCC | CGGGAGGAGC | TCGCCGCGCC | CGCTCGCCGC | 180 |
| CTCGTCTCCC | AGCGGCGGCG | GGAGGCGCGT | CTCCCCGGCC | CAGTCCGCGC | CCGGCCCCGC | 240 |
| GGGACCGCTC | CGGCCCGCTC | CGAGGAAAAA | CTGCATAGAA | AATCTAATGG | ATGAAGATGA | 300 |

| | | | | | | |
|---|---|---|---|---|---|---|
| GAAAGACAGA | GCCAAGAGAG | CTTCTCGAAA | CAAGTCTGAG | AAGAAGCGTC | GGGACCAGTT | 360 |
| CAATGTTCTC | ATCAAAGAGC | TCAGTTCCAT | GCTCCCTGGC | AACACGCGGA | AAATGGACAA | 420 |
| AACCACCGTG | TTGGAAAAGG | TCATCGGATT | TTTGCAGAAA | CACAATGAAG | TCTCAGCGCA | 480 |
| AACGGAAATC | TGTGACATTC | AGCAAGACTG | GAAGCCTTCA | TTCCTCAGTA | ATGAAGAATT | 540 |
| CACCCAGCTG | ATGTTGGAGG | CATTAGATGG | CTTCATTATC | GCAGTGACAA | CAGACGGCAG | 600 |
| CATCATCTAT | GTCTCTGACA | GTATCACGCC | TCTCCTTGGG | CATTTACCGT | CGGATGTCAT | 660 |
| GGATCAGAAT | TTGTTAAATT | TCCTCCCAGA | ACAAGAACAT | TCAGAAGTTT | ATAAAATCCT | 720 |
| TTCTTCCCAT | ATGCTTGTGA | CGGATTCCCC | CTCCCCAGAA | TACTTAAAAT | CTGACAGCGA | 780 |
| TTTAGAGTTT | TATTGCCATC | TTCTCAGAGG | CAGCTTGAAC | CCAAAGGAAT | TTCCAACTTA | 840 |
| TGAATACATA | AAATTTGTAG | GAAATTTTCG | CTCTTACAAC | AATGTGCCTA | GCCCTCCTG | 900 |
| TAATGGTTTT | GACAACACCC | TTTCAAGACC | TTGCCGGGTA | CCACTAGGAA | AGGAGGTTTG | 960 |
| CTTCATTGCC | ACCGTTCGTC | TGGCAACACC | ACAATTCTTA | AAGGAAATGT | GCATAGTTGA | 1020 |
| CGAACCTTTA | GAGGAATTCA | CTTCAAGGCA | TAGCTTGGAA | TGGAAATTTT | TATTTCTGGA | 1080 |
| TCACAGAGCA | CCTCCAATCA | TAGGATACCT | GCCTTTTGAA | GTGCTGGGAA | CCTCAGGCTA | 1140 |
| TGACTACTAC | CACATTGATG | ACCTGGAGCT | CCTGGCCAGG | TGTCACCAGC | ACCTGATGCA | 1200 |
| GTTTGGCACA | GGGAAGTCGT | GTTGCTACCG | GTTTCTGACC | AAAGGTCAGC | AGTGGATCTG | 1260 |
| GCTGCAGACT | CACTACTACA | TCACCTACCA | TCAGTGGAAC | TCCAAGCCCG | AGTTCATCGT | 1320 |
| GTGCACACAC | TCGGTGGTCA | GTTACGCAGA | TGTCCGGGTG | GAAAGGAGGC | AGGAGCTGGC | 1380 |
| TCTGGAAGAC | CCGCCATCCG | AGGCCCTCCA | CTCCTCAGCA | CTAAAGGACA | AGGGCTCAAG | 1440 |
| CCTGGAACCT | CGGCAGCACT | TTAACGCACT | CGACGTGGGT | GCCTCGGGCC | TTAATACCAG | 1500 |
| TCATTCGCCA | TCGGCGTCCT | CAAGAAGTTC | CCACAAATCC | TCGCACACAG | CCATGTCAGA | 1560 |
| ACCCACCTCC | ACTCCCACCA | AGCTGATGGC | AGAGGCCAGC | ACCCGGCTT | TGCCAAGATC | 1620 |
| AGCCACCCTG | CCCCAAGAGT | TACCTGTCCC | CGGGCTCAGC | CAGGCAGCCA | CCATGCCGGC | 1680 |
| CCCTCTGCCT | TCCCCATTGT | CCTGCGACCT | CACACAGCAG | CTCCTGCCTC | AGACCGTTCT | 1740 |
| GCAGAGCACG | CCCGCTCCCA | TGGCACAGTT | TTCGGCACAG | TTCAGCATGT | TCCAGACCAT | 1800 |
| CAAAGACCAG | CTAGAGCAGC | GGACGCGGAT | CCTGCAGGCC | AATATCCGGT | GGCAACAGGA | 1860 |
| AGAGCTCCAC | AAGATCCAGG | AGCAGCTCTG | CCTGGTCCAG | GACTCCAACG | TCCAGATGTT | 1920 |
| CCTGCAGCAG | CCAGCTGTAT | CCCTGAGCTT | CAGCAGCACC | CAGCGACCTG | AGGCTCAGCA | 1980 |
| GCAGCTACAG | CAAAGGTCAG | CTGCAGTGAC | TCAGCCCCAG | CTCGGGGCGG | GCCCCAACT | 2040 |
| TCCAGGGCAG | ATCTCCTCTG | CCCAGGTCAC | AAGCCAGCAC | CTGCTCAGAG | AATCAAGTGT | 2100 |
| GATATCAACC | CAAGGTCCAA | AGCCAATGAG | AAGCTCACAG | CTAATGCAGA | GCAGCGGCCG | 2160 |
| CTCTGGAAGC | AGCCTAGTGT | CCCCGTTCAG | CAGCGCCACA | GCTGCGCTCC | CGCCAAGTCT | 2220 |
| GAATCTGACC | ACACCTGCTT | CCACCTCCCA | GGATGCCAGC | CAGTGCCAGC | CCAGCCAGA | 2280 |
| CTTCAGCCAT | GATCGGCAGC | TCAGGCTGTT | GCTGAGCCAG | CCCATCCAGC | CCATGATGCC | 2340 |
| CGGGTCCTGT | GACGCAAGGC | AGCCCTCGGA | AGTCAGCAGG | ACGGACGGC | AAGTCAAGTA | 2400 |
| CGCCCAGAGC | CAGACCGTGT | TTCAAAATCC | AGACGCACAC | CCCGCCAACA | GCAGCAGCGC | 2460 |
| CCCGATGCCC | GTCCTGCTGA | TGGGCAGGC | GGTGCTCCAC | CCCAGCTTCC | CTGCCTCCCA | 2520 |
| ACCATCGCCC | CTGCAGCCTG | CACAGGCCCG | GCAGCAGCCA | CCGCAGCACT | ACCTGCAGGT | 2580 |
| ACAGGCACCA | ACCTCTTTGC | ACAGTGAGCA | GCAGGACTCG | CTACTTCTCT | CCACCTACTC | 2640 |
| ACAACAGCCA | GGGACCCTGG | GCTACCCCCA | ACCACCCCCA | GCACAGCCCC | AGCCCCTACG | 2700 |

-continued

| | | | | | | |
|---|---|---|---|---|---|---|
| TCCTCCCCGA | AGGGTCAGCA | GTCTGTCTGA | GTCGTCAGGC | CTCCAGCAGC | CGCCCCGATA | 2760 |
| ATGCCCCGGC | ACTGAAGTCG | GGACACAATC | AGCTTTAACC | AATGGATGAG | GGGGGTGGCC | 2820 |
| ACAGGAGATG | GGGAGAGGAG | TCTGAACTAA | ACCCCTGGCT | TTTGTGCACA | CTGCATACGT | 2880 |
| TTCAGAACTC | CTGGATGGTA | ACCATCTCTG | GAGTGCAGCG | CTTGCTGCAG | TGGAAATGAT | 2940 |
| CAGGAATACT | GACCGTGTTT | CTCTTGCCTC | CGAGGTTCTT | GGGCACACTC | TATAGCCATA | 3000 |
| CTGGACAGGA | ACCAGGTGCC | CCGTGTAGGC | ATCGTCGGTC | GGTTTGCCGT | CAGAGATGGC | 3060 |
| GCATCTCGCT | GCATCCCCCG | AGAGTACACC | GGTTGCTCTA | GCCACCTGCG | GCCCGCCCAT | 3120 |
| CTGCGCTAGC | TGGCCTTCAC | GCTCTTGATC | GTCTTTCCTT | TGTATTGGAG | AAGGACTGGG | 3180 |
| TCAGAGATCT | GTTGGAGAGA | GAGAATAAAG | AGATTATTTT | TCATTATTTT | TAAATGGTTG | 3240 |
| TTTTTGTTTT | AATTTGCACA | GCTACACAGA | GGAAATAACT | TAGGCACTTT | CTGTTTTTTT | 3300 |
| AAAAAAAATA | ATAAGGTCTC | ATGGCTTCAT | TCAGAGACCA | CAGTAACAAC | AGCAGCCCAC | 3360 |
| CAATCAGAGA | AGCTGGTTGT | TATTAACCAA | GCTACAGATT | CACACTTTCT | GGCCTAAACC | 3420 |
| CTAATGGGAT | GAGGCTTTTC | ACCCCAGGCC | ATGCTGGTGG | TGATTTTTTA | GCCCCTAAAT | 3480 |
| AAAACACTGG | ACTATTTCCT | GTTTACTTCA | TTGATTGCAA | CTACAAGGT | GGACTCAAAG | 3540 |
| CAAAGCACAA | TCATGCCAGC | CAACATTCCA | GAATTCTGCT | GAGAACTCCA | AGTCTGTGAG | 3600 |
| GGGAGAGGTT | TTACAAGCCA | GACAGGCCTG | GGGGACTGCA | GTCCCCAAGG | AGACCCTGCC | 3660 |
| ACATGCTGGC | CCTTTGAGTG | AGAATGCTGC | ATCTTTCTAC | ATATCTTCAT | GAGAATACTG | 3720 |
| AGAATTGGAT | TTTCCTTTTC | AAAATGCACT | TTGCTTTTTT | TGTATGTTTT | GTTATGTTGA | 3780 |
| GATGTTTCTA | AAGAAAAGAT | TTTATGTAAT | TATAAGATGA | AGCGTAGTGA | ATTGTACAGC | 3840 |
| TGTTGTAATA | ATGACCTATT | TCTATATAAA | ATAAAATTGT | ATGGCTTATG | TGTAAATTAT | 3900 |
| TTTGTATCTG | AGATACCAGT | TCCTTTTCCC | AAATATAAAA | GTATAAAAGT | TTTCTTGTGT | 3960 |
| TTTTCTGTGA | GTGAAAATTT | TGTAATAAAT | TAACAAATTT | GTACTGTAAT | | 4010 |

(2) INFORMATION FOR SEQ ID NO:4:

(i) SEQUENCE CHARACTERISTICS:
        (A) LENGTH: 4184 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

| | | | | | | |
|---|---|---|---|---|---|---|
| GGCACGAGCG | GCACGAGCCG | CCCTGGGCTT | CGGGTCCTGC | CAACCGCTGC | AGCCAGACAG | 60 |
| ACGGTGGGCT | CCCGGAGCTG | CTCGCCAAGA | GAGAGGACTA | GGCACCCCAA | ACATCGGGAT | 120 |
| TCGGGGGTCC | TCCGAGGGTG | CTAGAGGGGT | ACTGCGTGCC | CGGACAGAAG | CTTTCAAGAT | 180 |
| TGCCCGCTGC | CCTTCCAGAG | CCCCACCGCA | GGCATCCCGA | AGCGTAGGGA | GCCCGGGACG | 240 |
| CCTGGAGAGT | GTGGTTGCCT | GGCCGGGCCC | TTGTGTCACT | ACGTTCCTGG | GTCTGACTTG | 300 |
| GCTTAGGGCT | GGACTGAAAG | CCCAGTCTTT | GTGCTTAGAC | AGCTCTGCGC | TCCTGGGACT | 360 |
| CCCCGGGTTG | GATGCTACAA | CATTGTTTTA | GTGGGAGGTG | TGCCCCCTCC | CCAAGTAGAG | 420 |
| GAGGGGTGCG | ACCTTGACTT | TTCTAAAAAG | CCACTTAGGG | TGGAAGCAG | GGGGCAGGGA | 480 |
| CAGGTACCAA | GAGGCTCAAT | TCAAAGCCAG | CCTCCCCCCT | CTGCCCGCCT | CTCCTTAACT | 540 |
| GCTTAAGCAG | GCAAGACTGC | ATAGAAACTC | TAATGGACGA | AGATGAGAAG | GATAGAGCAA | 600 |
| AGAGAGCCTC | TCGAAATAAG | TCTGAGAAGA | AGCGTCGGGA | CCAGTTCAAT | GTTCTCATCA | 660 |
| AAGAGCTCAG | CTCCATGCTC | CCTGGTAACA | CTCGGAAAAT | GGACAAAACC | ACCGTGCTGG | 720 |

```
AGAAGGTCAT CGGATTCTTG CAGAAACACA ATGAAGTCTC AGCACAAACA GAAATCTGTG       780
ACATCCAGCA GGACTGGAAG CCATCATTCC TCAGTAACGA AGAATTCACC CAGCTGATGT       840
TGGAGGCATT AGATGGCTTC GTCATCGTCG TGACAACAGA CGGCAGCATC ATCTATGTGT       900
CCGACAGTAT CACACCTCTC CTTGGACATT TACCGGCGGA TGTCATGGAT CAGAACTTGT       960
TAAATTTCCT TCCAGAGCAA GAACATTCCG AAGTTTATAA AATCCTTTCT TCCCATATGC      1020
TTGTGACGGA TTCCCCCTCC CCAGAATTCC TAAAATCTGA CAACGATTTA GAGTTTTATT      1080
GCCATCTTCT CAGAGGCAGC TTGAACCCAA AGGAATTTCC AACTTACGAA TATATAAAAT      1140
TTGTAGGAAA TTTTCGCTCT TACAACAATG TGCCTAGCCC CTCCTGTAAT GGCTTTGACA      1200
ACACCCTTTC AAGACCCTGC CATGTACCCC TAGGAAAGGA CGTCTGCTTC ATCGCCACCG      1260
TGCGCCTGGC AACCCCGCAG TTCTTAAAGG AAATGTGTGT AGCTGACGAA CCTTTAGAGG      1320
AATTCACTTC GAGGCATAGC TTGGAATGGA AATTTTTATT TCTGGATCAC AGAGCTCCTC      1380
CAATCATAGG ATACCTGCCC TTTGAAGTAC TTGGCACCTC AGGCTACAAC TACTACCACA      1440
TTGATGACCT GGAGCTCCTG GCCAGGTGCC ACCAGCATCT GATGCAGTTT GGCAAAGGGA      1500
AGTCGTGCTG TTACCGGTTT CTAACCAAAG GGCAGCAGTG GATTTGGTTG CAAACCCACT      1560
ACTACATCAC CTACCACCAA TGGAACTCCA AGCCTGAGTT CATCGTATGC ACACACTCAG      1620
TGGTCAGTTA CGCAGATGTT CGAGTGGAAA GGAGACAGGA GCTGGCTCTG GAAGACCCAC      1680
CCACAGAGGC CATGCACCCC TCTGCAGTGA AGGAAAAGGA CTCAAGCCTA GAGCCTCCAC      1740
AGCCCTTTAA TGCACTTGAC ATGGGCGCCT CAGGTCTTCC CAGCAGCCCT TCTCCATCAG      1800
CCTCCTCAAG GAGTTCCCAC AAGTCCTCAC ACACAGCCAT GTCAGAACCC ACCTCCACTC      1860
CAACCAAGCT GATGGCTGAG AACAGCACCA CAGCTTTGCC AAGACCGGCC ACCCTACCCC      1920
AGGAGTTACC AGTGCAGGGG CTCAGCCAGG CAGCCACAAT GCCGACTGCT CTGCATTCCT      1980
CAGCCTCCTG CGACCTCACA AAGCAACTCC TGCTGCAGAG CCTGCCTCAG ACCGGCTTGC      2040
AGAGTCCACC TGCTCCAGTG ACACAGTTTT CAGCACAATT CAGCATGTTC AGACCATTA      2100
AAGACCAACT GGAGCAGAGG ACACGGATCC TGCAGGCCAA CATTCGGTGG CAGCAGGAAG      2160
AGCTTCATAA GATCCAGGAA CAACTCTGCC TGGTCCAGGA CTCCAACGTC CAGATGTTTC      2220
TGCAGCAGCC AGCTGTGTCC CTGAGCTTCA GCAGTACGCA GCGACCAGCA GCTCAGCAGC      2280
AGCTGCAGCA AAGGCCCGCC GCACCGTCTC AGCCCCAGCT TGTGGTCAAC ACTCCACTGC      2340
AGGGGCAGAT CACATCCACC CAAGTCACAA ACCAGCACCT GCTCCGAGAA TCGAATGTGA      2400
TATCCGCCCA GGGTCCAAAG CCAATGAGAA GTTCCCAGCT GCTGCCTGCC AGCGGCCGTT      2460
CACTGAGCAG CCTGCCATCC CAGTTTAGCA GTACAGCTTC CGTGCTCCCG CCTGGCCTGA      2520
GCCTCACCAC GATTGCTCCC ACCCCTCAGG ATGACAGCCA GTGCCAGCCC AGCCCTGACT      2580
TCGGCCATGA TCGGCAGCTC AGGCTGTTGC TGAGCCAGCC CATCCAGCCT ATGATGCCTG      2640
GGTCCTGCGA TGCCAGGCAG CCCTCAGAAG TCAGCAGAAC TGGACGGCAA GTCAAGTATG      2700
CACAGAGCCA AGTGATGTTT CCAAGTCCAG ACTCACACCC TACCAACAGC AGCGCATCCA      2760
CCCCGGTCCT GCTCATGGGG CAGGCAGTAC TCCATCCCAG CTTCCCTGCT TCCCGGCCAT      2820
CGCCACTGCA GCCAGCACAG GCACAGCAGC AGCCACCACC CTATTTGCAG CACCAACAT      2880
CTCTGCACAG TGAGCAGCCG GACTCGCTCC TTCTCTCCAC CTTCTCCCAG CAGCCGGGAA      2940
CCCTGGGCTA TGCAGCCACA CAGTCTACAC CTCCGCAACC CCACGCCCC TCCCGCAGGG      3000
TCAGCCGGCT GTCAGAGTCC TAAGGTCTCC AGCAGCCATC AGGGTAATAC CCTGACACTG      3060
GAGTCCAGAC GCAACCAGCT TTAACCAATG GAAAACGGGG TTGGCCGTGG GAGATGGGAT      3120
```

```
GAAGCGTTTA   CGTGATTTTG   GCGCACCCTG   TATACATTTC   AGAACTCCTG   ATGGTAACGT         3180

GTCTGGAGTG   TGGCACTGGC   AGAATGGGGA   AAGAACAGGA   ATATTGGCCA   TGATTCTTTT         3240

GCCCTGGGCT   TCTTGGGCAT   CCGCTACAGC   CATACCAGAC   AGGAACCAAG   TGTCCCCGTG         3300

TTGGCACCGC   TTCCTGGTCT   ATTTGCAGAG   GTGGTACCCC   TCGCTGCCTC   CAGGAGAGAG         3360

CGCTCCAGGT   ACTCTACCGA   CTGAGACAGG   TCCCAAGCCC   TAACAGGCCT   TCACTCTCTT         3420

GATAGTCTTT   CCTTTACAGT   CAAGGACTAC   GTTAAAGGTC   TCTGGAGAGA   GTATAAAGAG         3480

ATTATTTTTC   ATCGTTTTTA   AAAGGTTTTG   TTTTAATTTG   CACACCTGTG   CACAAGGGAA         3540

ATAACTTAGG   CACTTTCGGA   GTTTGTGTTT   GTTTTGTTTT   GTTTAATAAG   GTCCCATGGC         3600

TTCTTTGGGA   ATCCACGATA   AGAAAAACAA   CCCCACCAAT   CAGATAGCGG   AGCCTGTTAT         3660

TTGAAGCTGC   AGAGCCACAC   CCTTGGCCTA   ACCCCTAGCA   GACTGAGGCT   CTCCCATGCC         3720

TACCAGGGGG   TGTTTTCCTT   CCTAAACAGA   ACACTGGATT   CTTCCTGTTA   ACTTCACCGA         3780

GAGTAGCTAC   AAAGGTGGAC   TTAGAGCCAA   GCACAATCTC   ACAACGATTC   CAGAATTCCC         3840

TAGAGACCTC   TTGGGGGGCA   ACGGGCAGGC   TGCATCTCCC   AGGAAAACCA   GGCAAGGGCC         3900

CGCCATCCTA   TGAGGCAGGC   CACCGCACCT   TTCCACTTCT   CTTCCCCATG   ATTCCGAAGA         3960

TTGGATTTTC   CTTTTCAGGA   TGCACTTTGC   TTTTTTTTTT   TTTTTTTTGT   ATGTTTTGTT         4020

ATGTCGAGGT   ATTTCTAAAG   AGAAGATTTT   ATATAATTAT   AAGAGGAAGT   GTAGTGAATT         4080

GTACAGCTGT   TGTAATAATG   ACCTATTTCT   ATAAAAAAAT   AAAATTGTAC   GGATTATGTG         4140

TAAAAAAAAA   AAAAAAAAAA   AACTCGAGGG   GGCCCGTACC   CAAT                           4184
```

( 2 ) INFORMATION FOR SEQ ID NO:5:

( i ) SEQUENCE CHARACTERISTICS:
        ( A ) LENGTH: 590 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met  Ala  Ala  Pro  Tyr  Pro  Gly  Ser  Gly  Gly  Gly  Ser  Glu  Val  Lys  Cys
  1               5                  10                      15

Val  Gly  Gly  Arg  Gly  Ala  Ser  Val  Pro  Trp  Asp  Phe  Leu  Pro  Gly  Leu
              20                  25                      30

Met  Val  Lys  Ala  Pro  Ser  Gly  Pro  Cys  Leu  Gln  Ala  Gln  Arg  Lys  Glu
              35                  40                      45

Lys  Ser  Arg  Asn  Ala  Ala  Arg  Ser  Arg  Arg  Gly  Lys  Glu  Asn  Leu  Glu
         50                      55                  60

Phe  Phe  Glu  Leu  Ala  Lys  Leu  Leu  Pro  Leu  Pro  Gly  Ala  Ile  Ser  Ile
 65                      70                  75                          80

Gln  Leu  Asp  Lys  Ala  Ser  Ile  Val  Arg  Leu  Ser  Val  Thr  Tyr  Leu  Arg
                   85                  90                      95

Leu  Arg  Arg  Phe  Ala  Ala  Leu  Gly  Ala  Pro  Pro  Trp  Gly  Leu  Arg  Ala
             100                 105                     110

Ala  Gly  Pro  Pro  Ala  Gly  Leu  Ala  Pro  Gly  Arg  Arg  Gly  Pro  Ala  Ala
             115                 120                     125

Leu  Val  Ser  Glu  Val  Phe  Glu  Gln  His  Leu  Gly  Gly  His  Ile  Leu  Gln
             130                 135                     140

Ser  Leu  Asp  Gly  Phe  Val  Phe  Ala  Leu  Asn  Gln  Glu  Gly  Lys  Phe  Leu
145                      150                 155                         160
```

```
Tyr Ile Ser Glu Thr Val Ser Ile Tyr Leu Gly Leu Ser Gln Val Glu
                165                 170                 175
Met Thr Gly Ser Ser Val Phe Asp Tyr Ile His Pro Gly Asp His Ser
            180                 185                 190
Glu Val Leu Glu Gln Leu Gly Leu Arg Thr Thr Thr Pro Gly Pro Pro
        195                 200                 205
Thr Pro Ser Ser Val Ser Ser Ser Ser Ser Ser Ser Ser Ser Leu Ala
    210                 215                 220
Asp Thr Pro Glu Ile Glu Ala Ser Leu Thr Lys Val Pro Pro Ser Ser
225                 230                 235                 240
Leu Val Gln Glu Arg Ser Phe Phe Val Arg Met Lys Ser Thr Leu Thr
                245                 250                 255
Lys Arg Gly Leu His Val Lys Ala Ser Gly Tyr Lys Val Ile His Val
            260                 265                 270
Thr Gly Arg Leu Arg Ala His Ala Leu Gly Leu Val Ala Leu Gly His
        275                 280                 285
Thr Leu Pro Pro Ala Pro Leu Ala Glu Leu Pro Leu His Gly His Met
    290                 295                 300
Ile Val Phe Arg Leu Ser Leu Gly Leu Thr Ile Leu Ala Cys Glu Ser
305                 310                 315                 320
Arg Val Ser Asp His Met Asp Leu Gly Pro Ser Glu Leu Val Gly Arg
                325                 330                 335
Ser Cys Tyr Gln Phe Val His Gly Gln Asp Ala Thr Arg Ile Arg Gln
            340                 345                 350
Ser His Val Asp Leu Leu Asp Lys Gly Gln Val Met Thr Gly Tyr Tyr
        355                 360                 365
Arg Trp Leu Gln Arg Ala Gly Gly Phe Val Trp Leu Gln Ser Val Ala
    370                 375                 380
Thr Val Ala Gly Ser Gly Lys Ser Pro Gly Glu His His Val Leu Trp
385                 390                 395                 400
Val Ser His Val Leu Ser Gln Ala Glu Gly Gly Gln Thr Pro Leu Asp
                405                 410                 415
Ala Phe Gln Leu Pro Ala Ser Val Ala Cys Glu Glu Ala Ser Ser Pro
            420                 425                 430
Gly Pro Glu Pro Thr Glu Pro Glu Pro Pro Thr Glu Gly Lys Gln Ala
        435                 440                 445
Val Pro Ala Glu Asn Glu Ala Pro Gln Thr Gln Gly Lys Arg Ile Lys
    450                 455                 460
Val Glu Pro Gly Pro Arg Glu Thr Lys Gly Ser Glu Asp Ser Gly Asp
465                 470                 475                 480
Glu Asp Pro Ser Ser His Pro Ala Thr Pro Arg Pro Glu Phe Thr Ser
                485                 490                 495
Val Ile Arg Ala Gly Val Leu Lys Gln Asp Pro Val Arg Pro Trp Gly
            500                 505                 510
Leu Ala Pro Pro Gly Asp Pro Pro Thr Leu Leu His Ala Gly Phe
        515                 520                 525
Leu Pro Pro Val Val Arg Gly Leu Cys Thr Pro Gly Thr Ile Arg Tyr
    530                 535                 540
Gly Pro Ala Glu Leu Gly Leu Val Tyr Pro His Leu Gln Arg Leu Gly
545                 550                 555                 560
Pro Gly Pro Ala Leu Pro Glu Ala Phe Tyr Pro Pro Leu Gly Leu Pro
                565                 570                 575
Tyr Pro Gly Pro Ala Gly Thr Arg Leu Pro Arg Lys Gly Asp
            580                 585                 590
```

( 2 ) INFORMATION FOR SEQ ID NO:6:

( i ) SEQUENCE CHARACTERISTICS:
        ( A ) LENGTH: 594 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Met Ala Thr Pro Tyr Pro Arg Ser Gly Gly Arg Gly Glu Val Lys Cys
 1               5                  10                  15
Gly Gly Gly Arg Gly Ala Gly Val Pro Trp Asp Phe Leu Pro Gly Leu
                20                  25                  30
Met Val Lys Ala Pro Pro Gly Pro Cys Leu Gln Ala Gln Arg Lys Glu
            35                  40                  45
Lys Ser Arg Asn Ala Ala Arg Trp Arg Arg Gly Lys Glu Asn Leu Glu
        50                  55                  60
Phe Phe Glu Leu Ala Lys Leu Leu Pro Leu Pro Gly Ala Ile Ser Ser
65                  70                  75                  80
Gln Leu Asp Lys Ala Ser Ile Val Arg Leu Ser Val Thr Tyr Leu Arg
                85                  90                  95
Leu Arg Arg Phe Ala Ala Leu Gly Ala Pro Pro Trp Gly Leu Arg Ala
                100                 105                 110
Val Gly Pro Pro Ala Gly Leu Ala Pro Gly Arg Arg Gly Pro Val Ala
            115                 120                 125
Leu Val Ser Glu Val Phe Glu Gln His Leu Gly Gly His Ile Leu Gln
        130                 135                 140
Ser Leu Asp Gly Phe Val Phe Ala Leu Asn Gln Glu Gly Lys Phe Leu
145                 150                 155                 160
Tyr Ile Ser Glu Thr Val Ser Ile Tyr Leu Gly Leu Ser Gln Val Glu
                165                 170                 175
Leu Thr Gly Ser Ser Val Phe Asp Tyr Ile His Pro Gly Asp His Ser
                180                 185                 190
Glu Val Leu Glu Gln Leu Gly Leu Arg Ala Ala Ser Ile Gly Pro Pro
            195                 200                 205
Thr Pro Pro Ser Val Ser Ser Ser Ser Ser Ser Ser Ser Ser Ser Leu
        210                 215                 220
Val Asp Thr Pro Glu Ile Glu Ala Ser Pro Thr Glu Ala Ser Pro Ala
225                 230                 235                 240
Phe Arg Ala Gln Glu Arg Ser Phe Phe Val Arg Met Lys Ser Thr Leu
                245                 250                 255
Thr Lys Arg Gly Leu Asn Val Lys Ala Ser Gly Tyr Lys Val Ile His
                260                 265                 270
Val Thr Gly Arg Leu Arg Ala Arg Ala Leu Gly Leu Val Ala Leu Gly
            275                 280                 285
His Thr Leu Pro Pro Ala Pro Leu Ala Glu Leu Pro Leu His Gly His
        290                 295                 300
Met Ile Val Phe Arg Leu Ser Leu Gly Leu Thr Ile Leu Ala Cys Glu
305                 310                 315                 320
Ser Arg Val Ser Asp His Met Asp Met Gly Pro Ser Glu Leu Val Gly
                325                 330                 335
Arg Ser Cys Tyr Gln Phe Val His Gly Gln Asp Ala Thr Arg Ile Arg
                340                 345                 350
```

| Gln | Ser | His | Leu | Asp | Leu | Leu | Asp | Lys | Gly | Gln | Val | Val | Thr | Gly | Tyr |
|---|---|---|---|---|---|---|---|---|---|---|---|---|---|---|---|
| | | 355 | | | | | 360 | | | | | 365 | | | |

| Tyr | Arg | Trp | Leu | Gln | Arg | Ala | Gly | Gly | Phe | Val | Trp | Leu | Gln | Ser | Val |
|---|---|---|---|---|---|---|---|---|---|---|---|---|---|---|---|
| | 370 | | | | 375 | | | | | 380 | | | | | |

| Ala | Thr | Val | Ala | Gly | Asn | Gly | Lys | Ser | Thr | Gly | Glu | His | His | Val | Leu |
|---|---|---|---|---|---|---|---|---|---|---|---|---|---|---|---|
| 385 | | | | | 390 | | | | | 395 | | | | | 400 |

| Trp | Val | Ser | His | Val | Leu | Ser | Asn | Ala | Glu | Gly | Ser | Gln | Thr | Pro | Leu |
|---|---|---|---|---|---|---|---|---|---|---|---|---|---|---|---|
| | | | | 405 | | | | | 410 | | | | | 415 | |

| Asp | Ala | Phe | Gln | Leu | Pro | Ala | Ile | Val | Ser | Gln | Glu | Glu | Pro | Ser | Arg |
|---|---|---|---|---|---|---|---|---|---|---|---|---|---|---|---|
| | | | 420 | | | | | 425 | | | | | 430 | | |

| Pro | Gly | Pro | Glu | Pro | Thr | Glu | Glu | Glu | Pro | Pro | Val | Asp | Gly | Lys | Gln |
|---|---|---|---|---|---|---|---|---|---|---|---|---|---|---|---|
| | | | 435 | | | | 440 | | | | | 445 | | | |

| Ala | Val | Pro | Ala | Asp | Gln | Asp | Lys | Asp | Lys | Asp | Pro | Gln | Ala | Arg | Gly |
|---|---|---|---|---|---|---|---|---|---|---|---|---|---|---|---|
| | 450 | | | | | 455 | | | | | 460 | | | | |

| Lys | Arg | Ile | Lys | Val | Glu | Ala | Ser | Pro | Lys | Glu | Ala | Arg | Gly | Ser | Glu |
|---|---|---|---|---|---|---|---|---|---|---|---|---|---|---|---|
| 465 | | | | | 470 | | | | | 475 | | | | | 480 |

| Asp | Ser | Gly | Glu | Glu | Glu | Leu | Ser | Asp | Pro | Pro | Ala | Pro | Pro | Arg | Pro |
|---|---|---|---|---|---|---|---|---|---|---|---|---|---|---|---|
| | | | | 485 | | | | | 490 | | | | | 495 | |

| Glu | Phe | Thr | Ser | Val | Ile | Arg | Ala | Gly | Ala | Leu | Lys | His | Asp | Pro | Val |
|---|---|---|---|---|---|---|---|---|---|---|---|---|---|---|---|
| | | | 500 | | | | | 505 | | | | | 510 | | |

| Leu | Pro | Trp | Gly | Leu | Thr | Thr | Pro | Gly | Asp | Pro | Ser | Pro | Ala | Leu | Leu |
|---|---|---|---|---|---|---|---|---|---|---|---|---|---|---|---|
| | | 515 | | | | | 520 | | | | | 525 | | | |

| His | Ala | Gly | Phe | Leu | Pro | Pro | Val | Val | Arg | Gly | Leu | Cys | Thr | Pro | Gly |
|---|---|---|---|---|---|---|---|---|---|---|---|---|---|---|---|
| | 530 | | | | | 535 | | | | | 540 | | | | |

| Thr | Ile | Arg | Tyr | Gly | Pro | Ala | Glu | Leu | Ser | Leu | Met | Tyr | Pro | His | Leu |
|---|---|---|---|---|---|---|---|---|---|---|---|---|---|---|---|
| 545 | | | | | 550 | | | | | 555 | | | | | 560 |

| His | Arg | Leu | Gly | Ala | Gly | Pro | Ser | Leu | Pro | Glu | Ala | Phe | Tyr | Pro | Thr |
|---|---|---|---|---|---|---|---|---|---|---|---|---|---|---|---|
| | | | | 565 | | | | | 570 | | | | | 575 | |

| Leu | Gly | Leu | Pro | Tyr | Pro | Gly | Pro | Thr | Gly | Thr | Arg | Val | Gln | Arg | Lys |
|---|---|---|---|---|---|---|---|---|---|---|---|---|---|---|---|
| | | | 580 | | | | | 585 | | | | | 590 | | |

| Gly | Asp |
|---|---|

( 2 ) INFORMATION FOR SEQ ID NO:7:

( i ) SEQUENCE CHARACTERISTICS:
( A ) LENGTH: 824 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

| Met | Asp | Glu | Asp | Glu | Lys | Asp | Arg | Ala | Lys | Arg | Ala | Ser | Arg | Asn | Lys |
|---|---|---|---|---|---|---|---|---|---|---|---|---|---|---|---|
| 1 | | | | 5 | | | | | 10 | | | | | 15 | |

| Ser | Glu | Lys | Lys | Arg | Arg | Asp | Gln | Phe | Asn | Val | Leu | Ile | Lys | Glu | Leu |
|---|---|---|---|---|---|---|---|---|---|---|---|---|---|---|---|
| | | | 20 | | | | | 25 | | | | | 30 | | |

| Ser | Ser | Met | Leu | Pro | Gly | Asn | Thr | Arg | Lys | Met | Asp | Lys | Thr | Thr | Val |
|---|---|---|---|---|---|---|---|---|---|---|---|---|---|---|---|
| | | | 35 | | | | | 40 | | | | | 45 | | |

| Leu | Glu | Lys | Val | Ile | Gly | Phe | Leu | Gln | Lys | His | Asn | Glu | Val | Ser | Ala |
|---|---|---|---|---|---|---|---|---|---|---|---|---|---|---|---|
| | | 50 | | | | | 55 | | | | | 60 | | | |

| Gln | Thr | Glu | Ile | Cys | Asp | Ile | Gln | Gln | Asp | Trp | Lys | Pro | Ser | Phe | Leu |
|---|---|---|---|---|---|---|---|---|---|---|---|---|---|---|---|
| 65 | | | | | 70 | | | | | 75 | | | | | 80 |

| Ser | Asn | Glu | Glu | Phe | Thr | Gln | Leu | Met | Leu | Glu | Ala | Leu | Asp | Gly | Phe |
|---|---|---|---|---|---|---|---|---|---|---|---|---|---|---|---|
| | | | | 85 | | | | | 90 | | | | | 95 | |

| Ile | Ile | Ala | Val | Thr | Thr | Asp | Gly | Ser | Ile | Ile | Tyr | Val | Ser | Asp | Ser |
|---|---|---|---|---|---|---|---|---|---|---|---|---|---|---|---|
| | | | | 100 | | | | | 105 | | | | | 110 | |

-continued

| | | | | | | | | | | | | | | |
|---|---|---|---|---|---|---|---|---|---|---|---|---|---|---|
| Ile | Thr | Pro 115 | Leu | Leu | Gly | His | Leu 120 | Pro | Ser | Asp | Val | Met 125 | Asp | Gln | Asn |
| Leu | Leu 130 | Asn | Phe | Leu | Pro | Glu 135 | Gln | Glu | His | Ser | Glu 140 | Val | Tyr | Lys | Ile |
| Leu | Ser 145 | Ser | His | Met | Leu 150 | Val | Thr | Asp | Ser | Pro 155 | Ser | Pro | Glu | Tyr | Leu 160 |
| Lys | Ser | Asp | Ser | Asp 165 | Leu | Glu | Phe | Tyr | Cys 170 | His | Leu | Leu | Arg | Gly 175 | Ser |
| Leu | Asn | Pro | Lys 180 | Glu | Phe | Pro | Thr | Tyr 185 | Glu | Tyr | Ile | Lys | Phe 190 | Val | Gly |
| Asn | Phe | Arg 195 | Ser | Tyr | Asn | Asn | Val 200 | Pro | Ser | Pro | Ser | Cys 205 | Asn | Gly | Phe |
| Asp | Asn 210 | Thr | Leu | Ser | Arg | Pro 215 | Cys | Arg | Val | Pro | Leu 220 | Gly | Lys | Glu | Val |
| Cys 225 | Phe | Ile | Ala | Thr | Val 230 | Arg | Leu | Ala | Thr | Pro 235 | Gln | Phe | Leu | Lys | Glu 240 |
| Met | Cys | Ile | Val | Asp 245 | Glu | Pro | Leu | Glu | Glu 250 | Phe | Thr | Ser | Arg | His 255 | Ser |
| Leu | Glu | Trp | Lys 260 | Phe | Leu | Phe | Leu | Asp 265 | His | Arg | Ala | Pro | Pro 270 | Ile | Ile |
| Gly | Tyr | Leu 275 | Pro | Phe | Glu | Val | Leu 280 | Gly | Thr | Ser | Gly | Tyr 285 | Asp | Tyr | Tyr |
| His | Ile 290 | Asp | Asp | Leu | Glu | Leu 295 | Leu | Ala | Arg | Cys | His 300 | Gln | His | Leu | Met |
| Gln 305 | Phe | Gly | Thr | Gly | Lys 310 | Ser | Cys | Cys | Tyr | Arg 315 | Phe | Leu | Thr | Lys | Gly 320 |
| Gln | Gln | Trp | Ile | Trp 325 | Leu | Gln | Thr | His | Tyr 330 | Tyr | Ile | Thr | Tyr | His 335 | Gln |
| Trp | Asn | Ser | Lys 340 | Pro | Glu | Phe | Ile | Val 345 | Cys | Thr | His | Ser | Val 350 | Val | Ser |
| Tyr | Ala | Asp 355 | Val | Arg | Val | Glu | Arg 360 | Arg | Gln | Glu | Leu | Ala 365 | Leu | Glu | Asp |
| Pro | Pro 370 | Ser | Glu | Ala | Leu | His 375 | Ser | Ser | Ala | Leu | Lys 380 | Asp | Lys | Gly | Ser |
| Ser 385 | Leu | Glu | Pro | Arg | Gln 390 | His | Phe | Asn | Ala | Leu 395 | Asp | Val | Gly | Ala | Ser 400 |
| Gly | Leu | Asn | Thr | Ser 405 | His | Ser | Pro | Ser | Ala 410 | Ser | Ser | Arg | Ser | Ser 415 | His |
| Lys | Ser | Ser | His | Thr 420 | Ala | Met | Ser | Glu | Pro 425 | Thr | Ser | Thr | Pro 430 | Thr | Lys |
| Leu | Met | Ala | Glu 435 | Ala | Ser | Thr | Pro 440 | Ala | Leu | Pro | Arg | Ser 445 | Ala | Thr | Leu |
| Pro | Gln 450 | Glu | Leu | Pro | Val | Pro 455 | Gly | Leu | Ser | Gln | Ala 460 | Ala | Thr | Met | Pro |
| Ala 465 | Pro | Leu | Pro | Ser | Pro 470 | Leu | Ser | Cys | Asp | Leu 475 | Thr | Gln | Gln | Leu | Leu 480 |
| Pro | Gln | Thr | Val | Leu 485 | Gln | Ser | Thr | Pro | Ala 490 | Pro | Met | Ala | Gln | Phe 495 | Ser |
| Ala | Gln | Phe | Ser | Met 500 | Phe | Gln | Thr | Ile | Lys 505 | Asp | Gln | Leu | Glu 510 | Gln | Arg |
| Thr | Arg | Ile 515 | Leu | Gln | Ala | Asn | Ile 520 | Arg | Trp | Gln | Gln | Glu 525 | Glu | Leu | His |
| Lys | Ile | Gln | Glu | Gln | Leu | Cys | Leu | Val | Gln | Asp | Ser | Asn | Val | Gln | Met |

|       |       |       |       | 530   |       |       |       |       | 535   |       |       |       |       | 540   |
|-------|-------|-------|-------|-------|-------|-------|-------|-------|-------|-------|-------|-------|-------|-------|
| Phe   | Leu   | Gln   | Gln   | Pro   | Ala   | Val   | Ser   | Leu   | Ser   | Phe   | Ser   | Ser   | Thr   | Gln   | Arg
| 545   |       |       |       |       | 550   |       |       |       |       | 555   |       |       |       |       | 560

Pro Glu Ala Gln Gln Gln Leu Gln Gln Arg Ser Ala Ala Val Thr Gln
            565                     570                     575

Pro Gln Leu Gly Ala Gly Pro Gln Leu Pro Gly Gln Ile Ser Ser Ala
            580                 585                 590

Gln Val Thr Ser Gln His Leu Leu Arg Glu Ser Ser Val Ile Ser Thr
        595                 600                 605

Gln Gly Pro Lys Pro Met Arg Ser Ser Gln Leu Met Gln Ser Ser Gly
    610                 615                 620

Arg Ser Gly Ser Ser Leu Val Ser Pro Phe Ser Ser Ala Thr Ala Ala
625                 630                 635                 640

Leu Pro Pro Ser Leu Asn Leu Thr Thr Pro Ala Ser Thr Ser Gln Asp
                645                 650                 655

Ala Ser Gln Cys Gln Pro Ser Pro Asp Phe Ser His Asp Arg Gln Leu
            660                 665                 670

Arg Leu Leu Leu Ser Gln Pro Ile Gln Pro Met Met Pro Gly Ser Cys
        675                 680                 685

Asp Ala Arg Gln Pro Ser Glu Val Ser Arg Thr Gly Arg Gln Val Lys
    690                 695                 700

Tyr Ala Gln Ser Gln Thr Val Phe Gln Asn Pro Asp Ala His Pro Ala
705                 710                 715                 720

Asn Ser Ser Ser Ala Pro Met Pro Val Leu Leu Met Gly Gln Ala Val
                725                 730                 735

Leu His Pro Ser Phe Pro Ala Ser Gln Pro Ser Pro Leu Gln Pro Ala
            740                 745                 750

Gln Ala Arg Gln Gln Pro Pro Gln His Tyr Leu Gln Val Gln Ala Pro
        755                 760                 765

Thr Ser Leu His Ser Glu Gln Gln Asp Ser Leu Leu Leu Ser Thr Tyr
        770                 775                 780

Ser Gln Gln Pro Gly Thr Leu Gly Tyr Pro Gln Pro Pro Ala Gln
785                 790                 795                 800

Pro Gln Pro Leu Arg Pro Pro Arg Arg Val Ser Ser Leu Ser Glu Ser
            805                 810                 815

Ser Gly Leu Gln Gln Pro Pro Arg
            820

( 2 ) INFORMATION FOR SEQ ID NO:8:

( i ) SEQUENCE CHARACTERISTICS:
        ( A ) LENGTH: 816 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Met Asp Glu Asp Glu Lys Asp Arg Ala Lys Arg Ala Ser Arg Asn Lys
1               5                   10                  15

Ser Glu Lys Lys Arg Arg Asp Gln Phe Asn Val Leu Ile Lys Glu Leu
            20                  25                  30

Ser Ser Met Leu Pro Gly Asn Thr Arg Lys Met Asp Lys Thr Thr Val
        35                  40                  45

Leu Glu Lys Val Ile Gly Phe Leu Gln Lys His Asn Glu Val Ser Ala
    50                  55                  60

```
Gln  Thr  Glu  Ile  Cys  Asp  Ile  Gln  Gln  Asp  Trp  Lys  Pro  Ser  Phe  Leu
 65             70                      75                           80

Ser  Asn  Glu  Glu  Phe  Thr  Gln  Leu  Met  Leu  Glu  Ala  Leu  Asp  Gly  Phe
                    85                  90                           95

Val  Ile  Val  Val  Thr  Thr  Asp  Gly  Ser  Ile  Ile  Tyr  Val  Ser  Asp  Ser
                   100                 105                 110

Ile  Thr  Pro  Leu  Leu  Gly  His  Leu  Pro  Ala  Asp  Val  Met  Asp  Gln  Asn
          115                 120                           125

Leu  Leu  Asn  Phe  Leu  Pro  Glu  Gln  Glu  His  Ser  Glu  Val  Tyr  Lys  Ile
     130                 135                      140

Leu  Ser  Ser  His  Met  Leu  Val  Thr  Asp  Ser  Pro  Ser  Pro  Glu  Phe  Leu
145                      150                      155                      160

Lys  Ser  Asp  Asn  Asp  Leu  Glu  Phe  Tyr  Cys  His  Leu  Leu  Arg  Gly  Ser
               165                      170                           175

Leu  Asn  Pro  Lys  Glu  Phe  Pro  Thr  Tyr  Glu  Tyr  Ile  Lys  Phe  Val  Gly
               180                      185                      190

Asn  Phe  Arg  Ser  Tyr  Asn  Asn  Val  Pro  Ser  Pro  Ser  Cys  Asn  Gly  Phe
          195                      200                      205

Asp  Asn  Thr  Leu  Ser  Arg  Pro  Cys  His  Val  Pro  Leu  Gly  Lys  Asp  Val
     210                 215                      220

Cys  Phe  Ile  Ala  Thr  Val  Arg  Leu  Ala  Thr  Pro  Gln  Phe  Leu  Lys  Glu
225                      230                 235                           240

Met  Cys  Val  Ala  Asp  Glu  Pro  Leu  Glu  Glu  Phe  Thr  Ser  Arg  His  Ser
               245                      250                           255

Leu  Glu  Trp  Lys  Phe  Leu  Phe  Leu  Asp  His  Arg  Ala  Pro  Pro  Ile  Ile
               260                      265                 270

Gly  Tyr  Leu  Pro  Phe  Glu  Val  Leu  Gly  Thr  Ser  Gly  Tyr  Asn  Tyr  Tyr
          275                      280                      285

His  Ile  Asp  Asp  Leu  Glu  Leu  Leu  Ala  Arg  Cys  His  Gln  His  Leu  Met
290                      295                      300

Gln  Phe  Gly  Lys  Gly  Lys  Ser  Cys  Cys  Tyr  Arg  Phe  Leu  Thr  Lys  Gly
305                      310                 315                           320

Gln  Gln  Trp  Ile  Trp  Leu  Gln  Thr  His  Tyr  Tyr  Ile  Thr  Tyr  His  Gln
               325                      330                           335

Trp  Asn  Ser  Lys  Pro  Glu  Phe  Ile  Val  Cys  Thr  His  Ser  Val  Val  Ser
               340                      345                      350

Tyr  Ala  Asp  Val  Arg  Val  Glu  Arg  Arg  Gln  Glu  Leu  Ala  Leu  Glu  Asp
          355                      360                      365

Pro  Pro  Thr  Glu  Ala  Met  His  Pro  Ser  Ala  Val  Lys  Glu  Lys  Asp  Ser
370                      375                      380

Ser  Leu  Glu  Pro  Pro  Gln  Pro  Phe  Asn  Ala  Leu  Asp  Met  Gly  Ala  Ser
385                      390                      395                      400

Gly  Leu  Pro  Ser  Ser  Pro  Ser  Pro  Ala  Ser  Ser  Arg  Ser  Ser  His
               405                      410                      415

Lys  Ser  Ser  His  Thr  Ala  Met  Ser  Glu  Pro  Thr  Ser  Pro  Thr  Lys
               420                      425                      430

Leu  Met  Ala  Glu  Asn  Ser  Thr  Thr  Ala  Leu  Pro  Arg  Pro  Ala  Thr  Leu
          435                      440                      445

Pro  Gln  Glu  Leu  Pro  Val  Gln  Gly  Leu  Ser  Gln  Ala  Ala  Thr  Met  Pro
450                      455                      460

Thr  Ala  Leu  His  Ser  Ser  Ala  Ser  Cys  Asp  Leu  Thr  Lys  Gln  Leu  Leu
465                      470                      475                      480

Leu  Gln  Ser  Leu  Pro  Gln  Thr  Gly  Leu  Gln  Ser  Pro  Pro  Ala  Pro  Val
```

|   |   |   |   | 485 |   |   |   |   | 490 |   |   |   | 495 |   |   |
|---|---|---|---|---|---|---|---|---|---|---|---|---|---|---|---|
| Thr | Gln | Phe | Ser<br>500 | Ala | Gln | Phe | Ser | Met<br>505 | Phe | Gln | Thr | Ile | Lys<br>510 | Asp | Gln |
| Leu | Glu | Gln<br>515 | Arg | Thr | Arg | Ile | Leu<br>520 | Gln | Ala | Asn | Ile | Arg<br>525 | Trp | Gln | Gln |
| Glu | Glu<br>530 | Leu | His | Lys | Ile | Gln<br>535 | Glu | Gln | Leu | Cys | Leu<br>540 | Val | Gln | Asp | Ser |
| Asn<br>545 | Val | Gln | Met | Phe | Leu<br>550 | Gln | Gln | Pro | Ala | Val<br>555 | Ser | Leu | Ser | Phe | Ser<br>560 |
| Ser | Thr | Gln | Arg | Pro<br>565 | Ala | Ala | Gln | Gln | Gln<br>570 | Leu | Gln | Gln | Arg | Pro<br>575 | Ala |
| Ala | Pro | Ser | Gln<br>580 | Pro | Gln | Leu | Val | Val<br>585 | Asn | Thr | Pro | Leu | Gln<br>590 | Gly | Gln |
| Ile | Thr | Ser<br>595 | Thr | Gln | Val | Thr | Asn<br>600 | Gln | His | Leu | Leu | Arg<br>605 | Glu | Ser | Asn |
| Val | Ile<br>610 | Ser | Ala | Gln | Gly | Pro<br>615 | Lys | Pro | Met | Arg | Ser<br>620 | Ser | Gln | Leu | Leu |
| Pro<br>625 | Ala | Ser | Gly | Arg | Ser<br>630 | Leu | Ser | Ser | Leu | Pro<br>635 | Ser | Gln | Phe | Ser | Ser<br>640 |
| Thr | Ala | Ser | Val | Leu<br>645 | Pro | Pro | Gly | Leu | Ser<br>650 | Leu | Thr | Thr | Ile | Ala<br>655 | Pro |
| Thr | Pro | Gln | Asp<br>660 | Asp | Ser | Gln | Cys | Gln<br>665 | Pro | Ser | Pro | Asp | Phe<br>670 | Gly | His |
| Asp | Arg | Gln<br>675 | Leu | Arg | Leu | Leu | Leu<br>680 | Ser | Gln | Pro | Ile | Gln<br>685 | Pro | Met | Met |
| Pro | Gly<br>690 | Ser | Cys | Asp | Ala | Arg<br>695 | Gln | Pro | Ser | Glu | Val<br>700 | Ser | Arg | Thr | Gly |
| Arg<br>705 | Gln | Val | Lys | Tyr | Ala<br>710 | Gln | Ser | Gln | Val | Met<br>715 | Phe | Pro | Ser | Pro | Asp<br>720 |
| Ser | His | Pro | Thr | Asn<br>725 | Ser | Ser | Ala | Ser | Thr<br>730 | Pro | Val | Leu | Leu | Met<br>735 | Gly |
| Gln | Ala | Val | Leu<br>740 | His | Pro | Ser | Phe | Pro<br>745 | Ala | Ser | Arg | Pro | Ser<br>750 | Pro | Leu |
| Gln | Pro | Ala<br>755 | Gln | Ala | Gln | Gln | Gln<br>760 | Pro | Pro | Pro | Tyr | Leu<br>765 | Gln | Ala | Pro |
| Thr | Ser<br>770 | Leu | His | Ser | Glu | Gln<br>775 | Pro | Asp | Ser | Leu | Leu<br>780 | Leu | Ser | Thr | Phe |
| Ser<br>785 | Gln | Gln | Pro | Gly | Thr<br>790 | Leu | Gly | Tyr | Ala | Ala<br>795 | Thr | Gln | Ser | Thr | Pro<br>800 |
| Pro | Gln | Pro | Pro | Arg<br>805 | Pro | Ser | Arg | Arg | Val<br>810 | Ser | Arg | Leu | Ser | Glu<br>815 | Ser |

What is claimed is:

1. A recombinant nucleic acid encoding a neuronal PAS domain protein (NPAS) comprising SEQ ID NO:5, 6, 7 or 8.

2. An isolated cell comprising a nucleic acid according to claim 1.

3. A method of making an isolated NPAS protein, comprising steps: introducing a nucleic acid according to claim 1 into an isolated host cell or cellular extract, incubating said host cell or extract under conditions whereby said nucleic acid is expressed as a transcript and said transcript is translated as a translation product comprising said protein, and isolating said translation product.

4. An isolated NPAS nucleic acid comprising SEQ ID NO:1, 2, 3 or 4.

* * * * *